US008198240B2

(12) United States Patent
Yeomans et al.

(10) Patent No.: US 8,198,240 B2
(45) Date of Patent: *Jun. 12, 2012

(54) METHODS FOR TREATMENT OF HEADACHES BY ADMINISTRATION OF OXYTOCIN

(75) Inventors: David C. Yeomans, Sunnyvale, CA (US); Martin S. Angst, Palo Alto, CA (US); William H. Frey, II, White Bear Lake, MN (US); Daniel I. Jacobs, Mountain View, CA (US)

(73) Assignees: The Board of Trustees of the Leland Stanford Junior University, Palo Alto, CA (US); Trigemina, Inc., Mountain View, CA (US); HealthPartners Research Foundation, Bloomington, MN (US)

( * ) Notice: Subject to any disclaimer, the term of this patent is extended or adjusted under 35 U.S.C. 154(b) by 229 days.

This patent is subject to a terminal disclaimer.

(21) Appl. No.: 12/210,866

(22) Filed: Sep. 15, 2008

(65) Prior Publication Data
US 2009/0181880 A1    Jul. 16, 2009

Related U.S. Application Data

(63) Continuation of application No. 11/511,997, filed on Aug. 28, 2006, now abandoned.

(60) Provisional application No. 60/711,950, filed on Aug. 26, 2005, provisional application No. 60/794,004, filed on Apr. 21, 2006.

(51) Int. Cl.
A61K 38/11   (2006.01)
A61K 51/00   (2006.01)
A61P 5/10    (2006.01)
C07K 7/16    (2006.01)

(52) U.S. Cl. ..................... 514/11.6; 530/315
(58) Field of Classification Search .............. None
See application file for complete search history.

(56) References Cited

U.S. PATENT DOCUMENTS

| | | | |
|---|---|---|---|
| 2,938,891 A | 5/1960 | Velluz et al. |
| 3,076,797 A | 2/1963 | Velluz at al. |
| 4,213,968 A | 7/1980 | Kastin et al. |
| 4,464,378 A | 8/1984 | Hussain |
| 4,486,441 A | 12/1984 | Fozard et al. |
| 4,885,287 A | 12/1989 | Hussain et al. |
| 5,624,898 A | 4/1997 | Frey, II |
| 5,656,721 A | 8/1997 | Albert et al. |
| 5,859,048 A | 1/1999 | Oohashi et al. |
| 6,054,462 A | 4/2000 | Francois et al. |
| 6,090,368 A | 7/2000 | Zia et al. |
| 6,139,861 A | 10/2000 | Friedman |
| 6,143,278 A | 11/2000 | Elkhoury |
| 6,166,039 A | 12/2000 | Yaksh |
| 6,180,603 B1 | 1/2001 | Frey, II |
| 6,262,021 B1 | 7/2001 | Uvnas-Moberg et al. |
| 6,313,093 B1 | 11/2001 | Frey, II |
| 6,342,478 B1 | 1/2002 | Frey, II |
| 6,407,061 B1 | 6/2002 | Frey, II |
| 6,413,499 B1 | 7/2002 | Clay |
| 6,677,346 B1 | 1/2004 | Achari et al. |
| 6,815,424 B2 | 11/2004 | Vickery et al. |
| 6,825,203 B2 | 11/2004 | Pasternak et al. |
| 6,881,423 B2 | 4/2005 | Dohi et al. |
| 6,991,785 B2 | 1/2006 | Frey, II |
| 7,273,618 B2 | 9/2007 | Frey, II et al. |
| 7,452,868 B2 | 11/2008 | Kuzma et al. |
| 2001/0043915 A1 | 11/2001 | Frey, II |
| 2001/0055607 A1 | 12/2001 | Levin |
| 2002/0028786 A1 | 3/2002 | Frey, II et al. |
| 2002/0072498 A1 | 6/2002 | Frey, II |
| 2002/0082215 A1 | 6/2002 | Frey, II |
| 2002/0141971 A1 | 10/2002 | Frey, II |
| 2002/0169102 A1 | 11/2002 | Frey, II |
| 2003/0072793 A1 | 4/2003 | Frey, II et al. |
| 2003/0077300 A1 | 4/2003 | Wermeling |
| 2003/0104085 A1 | 6/2003 | Yeomans |
| 2003/0119892 A1 | 6/2003 | Caldwell et al. |
| 2003/0165434 A1 | 9/2003 | Reinhard et al. |
| 2003/0185872 A1 | 10/2003 | Kochinke |
| 2003/0215398 A1 | 11/2003 | Frey, II |
| 2003/0223981 A1 | 12/2003 | Mochly-Rosen et al. |
| 2003/0229025 A1 | 12/2003 | Xiao et al. |
| 2004/0105889 A1 | 6/2004 | Ryde et al. |
| 2004/0120896 A1 | 6/2004 | Dugger, III |
| 2004/0204366 A1 | 10/2004 | Pasternak et al. |
| 2004/0258757 A1 | 12/2004 | Bosch et al. |
| 2005/0142072 A1 | 6/2005 | Birch et al. |
| 2005/0153885 A1 | 7/2005 | Yun et al. |

(Continued)

FOREIGN PATENT DOCUMENTS

| | | |
|---|---|---|
| DE | 43 12 913 A1 | 10/1994 |
| EP | 1 468 690 A1 | 10/2004 |
| EP | 1 928 484 B1 | 6/2008 |
| JP | 2001-2589 A | 1/2001 |
| JP | 2001-89359 A | 4/2001 |
| JP | 2001-527537 A | 12/2001 |
| JP | 2005-500258 A | 1/2005 |
| JP | 2009-506071 A | 2/2009 |
| JP | 2009-506076 A | 2/2009 |
| WO | WO-86/06959 A1 | 12/1986 |

(Continued)

OTHER PUBLICATIONS

Combination therapy for headaches. http://www.headachedrugs.com/archives2/combination.html.*
Zubrzycka et al. (Inhibition of trigemino-hypoglossal reflex in rats by oxytocin is mediated by mu and kappa opioid receptors. Brain Res. Feb. 21, 2005;1035(1):67-72.*
Aboufatima, R. et al. (Apr. 8, 2004). "No Tolerance to the Antinociceptive Action of Calcitonin in Rats and Mice," *Neurosci. Lett.* 359(1-2):5-8.

(Continued)

Primary Examiner — Maury Audet
(74) Attorney, Agent, or Firm — Morrison & Foerster LLP

(57) ABSTRACT

The present invention relates to methods for the treatment of headache and headache disorders. The methods comprise administration of an oxytocin peptide for the treatment of primary and secondary headaches or trigeminal neuralgia.

17 Claims, 4 Drawing Sheets

U.S. PATENT DOCUMENTS

| | | | |
|---|---|---|---|
| 2005/0272642 A1 | 12/2005 | Frey et al. | |
| 2006/0009413 A1 | 1/2006 | Frey, II et al. | |
| 2006/0009414 A1 | 1/2006 | Frey, II et al. | |
| 2006/0014716 A1 | 1/2006 | Frey, II et al. | |
| 2006/0030542 A1 | 2/2006 | Frey, II et al. | |
| 2006/0039995 A1 | 2/2006 | Frey, II et al. | |
| 2006/0135437 A1* | 6/2006 | Stoehr et al. | 514/19 |
| 2006/0159626 A1 | 7/2006 | Frey, II | |
| 2006/0188496 A1 | 8/2006 | Bentz et al. | |
| 2006/0216317 A1 | 9/2006 | Reinhard et al. | |
| 2006/0252685 A1* | 11/2006 | Gould | 514/12 |
| 2007/0004743 A1 | 1/2007 | Xiao et al. | |
| 2007/0054843 A1 | 3/2007 | Yeomans et al. | |
| 2007/0093420 A1 | 4/2007 | Yeomans et al. | |
| 2009/0291900 A1 | 11/2009 | Yeomans et al. | |
| 2009/0317377 A1 | 12/2009 | Yeomans et al. | |
| 2010/0080797 A1 | 4/2010 | Yeomans et al. | |

FOREIGN PATENT DOCUMENTS

| | | |
|---|---|---|
| WO | WO-91/07947 A1 | 6/1991 |
| WO | WO-93/15737 A1 | 8/1993 |
| WO | WO-93/17037 A1 | 9/1993 |
| WO | WO-94/21286 A1 | 9/1994 |
| WO | WO-98/42275 A1 | 10/1998 |
| WO | WO-98/43660 A1 | 10/1998 |
| WO | WO-00/33813 A1 | 6/2000 |
| WO | WO-00/33814 A2 | 6/2000 |
| WO | WO-00/33814 A3 | 6/2000 |
| WO | WO-01/41732 A1 | 6/2001 |
| WO | WO-02/076388 A2 | 10/2002 |
| WO | WO-02/076388 A3 | 10/2002 |
| WO | WO-02/082074 A1 | 10/2002 |
| WO | WO-02/086105 A1 | 10/2002 |
| WO | WO-03/072056 A1 | 9/2003 |
| WO | WO-03/093816 A2 | 11/2003 |
| WO | WO-03/093816 A3 | 11/2003 |
| WO | WO-2004/019875 A2 | 3/2004 |
| WO | WO-2004/019875 A3 | 3/2004 |
| WO | WO-2004/043428 A2 | 5/2004 |
| WO | WO-2004/043428 A3 | 5/2004 |
| WO | WO-2004/062563 A2 | 7/2004 |
| WO | WO-2004/062563 A3 | 7/2004 |
| WO | WO-2004/093897 A1 | 11/2004 |
| WO | WO-2005/115370 A2 | 12/2005 |
| WO | WO-2005/115370 A3 | 12/2005 |
| WO | WO-2006/020727 A2 | 2/2006 |
| WO | WO-2006/091332 A2 | 8/2006 |
| WO | WO-2006/091332 A3 | 8/2006 |
| WO | WO-2007/025249 A2 | 3/2007 |
| WO | WO-2007/025249 A3 | 3/2007 |
| WO | WO-2007/025286 A2 | 3/2007 |
| WO | WO-2007/025286 A3 | 3/2007 |

OTHER PUBLICATIONS

Abouleish, E. (Nov.-Dec. 1976). "Postpartum Hypertension and Convulsion After Oxytocic Drugs," *Anesth. Analg.* 55(6):813-815.

Ågren, G. et al. (Sep. 29, 1997). "Olfactory Cues from an Oxytocin-Injected Male Rat can Induce Anti-Nociception in its Cagemates," *Neuroreport* 8(14):3073-3076.

Agu, R.U. et al. (2004). "Metabolism and Absorption Enhancement of Methionine Enkephalin in Human Nasal Epithelium," *Peptides* 25:563-569.

Amico, J.A. et al. (Nov. 1983). "A Time-Dependent Peak of Oxytocin Exists in Cerebrospinal Fluid but Not in Plasma of Humans," *J. Clin. Endocrinol. Metab.* 57(5):947-951.

Arletti, R. et al. (Mar. 1993). "Influence of Oxytocin on Nociception and Morphine Antinociception," *Neuropeptides* 24(3):125-129.

Beck, E. et al. (Feb. 15, 2005). "Management of Cluster Headache," *American Family Physician* 71(4):717-724.

Bessette, L. et al. (1998). "A Placebo Controlled Crossover Trial of Subcutaneous Salmon Calcitonin in the Treatment of Patients with Fibromyalgia," *Scand. J. Rheumatol.* 27(2):112-116.

Born, J. et al. (Jun. 2002). "Sniffing Neuropeptides: A Transnasal Approach to the Human Brain," *Nat. Neurosci.* 5(6):514-516.

Braga, P.C. et al. (Mar. 5, 1993). "Antinociceptive Activity of Salmon Calcitonin: Electrophysiological Correlates in a Rat Chronic Pain Model," *Neurosci. Lett.* 151(1):85-88.

Calvin, W.H. et al. (Apr. 1977). "A Neurophysiological Theory for the Pain Mechanism of Tic Douloureux," *Pain* 3(2):147-154.

Candeletti, S. et al. (Feb. 1992). "Intracerebroventricular Salmon Calcitonin Reduces Autotomy Behavior in Rats After Dorsal Rhizotomy," *Pain* 48(2):275-278.

Carlton, S.M. et al. (Jun. 1, 2001). "Tonic Control of Peripheral Cutaneous Nociceptors by Somatostatin Receptors," *J. Neurosci.* 21(11):4042-4049.

Carlton, S.M. et al. (2004). "Somatostatin Modulates the Transient Receptor Potential Vanilloid 1 (TRPV1) Ion Channel," *Pain* 110(3):616-627.

Carr, D.B. et al. (2004). "Safety and Efficacy of Intranasal Ketamine for the Treatment of Breakthrough Pain in Patients with Chronic Pain; a Randomized, Double-Blind, Placebo-Controlled, Crossover Study," *Pain* 108(1-2):17-27.

Carstens, J.H. Jr. et al. (1991). "Future Horizons for Calcitonin: A U.S. Perspective," *Calcif. Tissue Int.* 49(Suppl. 2):S2-S6.

Chevillard, C. et al. (1984). "Angiotensin-Converting Enzyme in Discrete Forebrain Areas of Spontaneously Hypertensive Rats," *Brain Research* 309:389-392.

Condés-Lara, M. et al. (Jun. 20, 2003). "Actions of Oxytocin and Interactions with Glutamate on Spontaneous and Evoked Dorsal Spinal Cord Neuronal Activities," *Brain Res.* 976(1):75-81.

Condés-LAra, M. et al. (May 31, 2005). "Oxytocin Actions on Afferent Evoked Spinal Cord Neuronal Activities in Neuropathic but not in Normal Rats," *Brain Res.* 1045(1-2):124-133.

Condés-Lara, M. et al. (Apr. 7, 2006). "Paraventricular Hypothalamic Influences on Spinal Nociceptive Processing," *Brain Res.* 1081(1):126-137.

Copp, D.H. (Jun. 1994). "Calcitonin: Discovery, Development, and Clinical Application," *Clin. Invest. Med.* 17(3):268-277.

De Fraissinette, A. et al. (Oct. 1995). "In vitro Tolerability of Human Nasal Mucosa: Histopathological and Scanning Electron-Microscopic Evlauation of Nasal Forms Containing Sandostatin®," *Cell Biol. Toxicol.* 11(5):295-301.

Eggers, T.R. et al. (Feb. 1979). "Water Intoxication and Syntocinon Infusion," *Aust. NZ J. Obstet Gynaecol.* 19(1):59-60.

Epperson, C.N. et al. (1996). "Intranasal Oxytocin in Obsessive-Compulsive Disorder," *Biol. Psychiatry* 40(6):547-549.

Epperson, C.N. et al. (1996). "Intranasal Oxytocin in Trichotillomania," *Biol. Psychiatry* 40(6):559-560.

Ezzat, S. et al. (Nov. 1, 1992). "Octreotide Treatment of Acromegaly. A Randomized, Multicenter Study," *Annals of Internal Medicine* 117(9):711-718.

Fabbri, A. et al. (Sep. 23, 1985). "Calcitonin Receptors in the Rat Mesencephalon Mediate its Analgesic Actions: Autoradiographic and Behavioral Analyses," *Brain Res.* 343(2):205-215.

Fassler, J.E. et al. (1990). "Octreotide Inhibits Increases in Short-Circuit Current Induced in Rat Colon by VIP, Substance P, Serotonin and Aminophylline," *Regulatory Peptides* 29(2-3):189-197.

Fischer, M.J.M. et al. (Jun. 22, 2005). "The Nonpeptide Calcitonin Gene-Related Peptide Receptor Antagonist BIBN4096BS Lowers the Activity of Neurons with Meningeal Input in the Rat Spinal Trigeminal Nucleus," *The Journal of Neuroscience* 25(25):5877-5883.

Flood, P. et al. (Dec. 2004). "Intranasal Nicotine for Postoperative Pain Treatment," *Anesthesiology* 101(6):1417-1421.

Frey, W.H. II (Jul./Aug. 2002). "Bypassing the Blood-Brain Barrier to Deliver Therapeutic Agents to the Brain and Spinal Cord," *Drug Delivery Technology* 2(5):46-49.

Gabopoulou, Z. et al. (Dec. 2002). "Epidural Calcitonin: Does it Provide Better Postoperative Analgesia? An Analysis of the Haemodynamic, Endocrine, and Nociceptive Responses of Salmon Calcitonin and Opioids in Epidural Anesthesia for Hip Arthroplasty Surgery," *Pain Pract.* 2(4):326-331.

Gaginella, T.S. et al. (Sep. 1990). "Treatment of Endocrine and Nonendocrine Secretory Diarrheal States with Sandostatin," *Metabolism: Clinical and Experimental* 39(9 Suppl 2):172-175.

Gazelius, B. et al. (1981). "Evidence that Substance P is a Mediator of Antidromic Vasodilatation Using Somatostatin as a Release Inhibitor," *Acta Physiologica Scandinavica* 113(2):155-159.

Ge, Y. et al. (Feb. 15, 2002). "Blockade Effect of mu and kappa Opioid Antagonists on the Anti-Nociception Induced by Intra-Periaqueductal Grey Injection of Oxytocin in Rats," *Brain Res.* 927(2):204-207.

Ghai, B. et al. (Dec. 2004). "Complex Regional Pain Syndrome: A Review," *J. Postgraduate Medicine* 50(4):300-307.

Gimpl, G. et al. (Apr. 2001). "The Oxytocin Receptor System: Structure, Function and Regulation," *Physiol. Rev.* 81(2):629-683.

Goadsby, P.J. (2005). "New Targets in the Acute Treatment of Headache," *Current Opinion in Neurology* 18(3):283-288.

Goadsby, P.J. (Apr. 2005). "Migrain Pathophysiology," *Headache* 45(Suppl.1):S14-S24.

Gobelet, C. et al. (Sep. 1986). "Calcitonin and Reflex Sympathetic Dystrophy Syndrome," *Clin. Rheumatol.* 5(3):382-388.

Goodlin, R.C. (Dec. 15, 1985). "Is Oxytocin the Culprit?" *Am. J. Obstet Gynecol.* 153(8):928-929.

Guidobono, F. et al. (Mar.-Apr. 1986). "Eel Calcitonin Binding Site Distribution and Antinociceptive Activity in Rats," *Peptides* 7(2):315-322.

Gupta, D.R. et al. (May 1, 1972). "Oxytocin, 'Salting Out,' and Water Intoxication," *JAMA* 220(5):681-683.

Gwak, H.S. et al. (2003). "Analgesic Effects of Intra-Nasal Enkephalins," *Journal of Pharmacy and Pharmacology* 55:1207-1212.

Hackler, L. et al. (1997). "Isolation of Relatively Large Amounts of Endomorphin-1 and Endomorphin-2 From Human Brain Cortex," *Peptides* 18(10):1635-1639.

Haldemann, A.R. et al. (Mar. 1995). "Somatostatin Receptor Scintigraphy in Central Nervous System Tumors: Role of Blood-Brain Barrier Permeability," *J. Nucl. Med.* 36(3):403-410.

Hamamci, N. et al. (Oct.-Nov. 1996). "Calcitonin Treatment in Reflex Sympathetic Dystrophy: A Preliminary Study," *Br. J. Clin. Pract.* 50(7):373-375.

Harris, R.E. (Jun. 1970). "Water Intoxication Secondary to Oxytocin," *VA Med. Mon.* 97(6):357-359.

Heinrichs, M. et al. (Oct. 30, 2004). "Selective Amnesic Effects of Oxytocin on Human Memory," *Physiol Behav.* 83(1):31-38.

Helmchen, C. et al. (1995). "Inhibition of Spinal Nociceptive Neurons by Microinjections of Somatostatin into the Nucleus Raphe Magnus and the Midbrain Periaqueductal Gray of the Anesthetized Cat," *Neuroscience Letters* 187(2):137-141.

Helyes, Z. et al. (1996). "Anti-Inflammatory and Antinociceptive Effect of Different Somatostatin-Analogs," *Neurobiology* 4(1-2):115-117.

Helyes, Z. et al. (2000). "Anti-Nociceptive Effect Induced by Somatostatin Released from Sensory Nerve Terminals and by Synthetic Somatostatin Analogues in the Rat," *Neuroscience Letters* 278(3):185-188.

Helyes, Z. et al. (2001). "Anti-Inflammatory Effect of Synthetic Somatostatin Analogues in the Rat," *British Journal of Pharmacology* 134(7):1571-1579.

Helyes, Z. et al. (May 2004). "Antiinflammatory and Analgesic Effects of Somatostatin Released from Capsaicin-Sensitive Sensory Nerve Terminals in a Freund's Adjuvant-Induced Chronic Arthritis Model in the Rat," *Arthritis and Rheumatism* 50(5):1677-1685.

Hoover, R.T. (1971). "Intranasal Oxytocin in Eighteen Hundred Patients. A Study on its Safety as Used in a Community Hospital," *Am. J. Obstet. Gynecol.* 110(6):788-794.

Hruby, V.J. et al. (Jul.-Sep. 1989). "Recent Developments in the Design of Receptor Specific Opioid Peptides," *Medicinal Research Reviews* 9(3):343-401.

Hunter, D.D. et al. (1998). "Identification and Neuropeptide Content of Trigeminal Neurons Innervating the Rat Nasal Epithelium," *Neuroscience* 83(2):591-599.

Illum, L. (Jan. 2004). "Is Nose-To-Brain Transport of Drugs in Man a Reality?" *J. Pharm. Pharmacol.* 56(1):3-17.

International Search Report mailed on Feb. 16, 2007, for PCT Patent Application No. PCT/US2006/033500, filed on Aug. 28, 2006, four pages.

International Search Report mailed Mar. 2, 2007, for PCT Patent Application No. PCT/US2006/033672, filed Aug. 28, 2006, 6 pages.

Invitti, C. et al. (1996). "Effect of Chronic Treatment with Octreotide Nasal Powder on Serum Levels of Growth Hormone, Insulin-Like Growth Factor I, Insulin-Like Growth Factor Binding Proteins 1 and 3 in Acromegalic Patients," *J. Endocrino. Invest.* 19(8):548-555.

Jaeger, H. et al. (Jan. 1992). "Calcitonin in Phantom Limb Pain: a Double-Blind Study," *Pain* 48(1):21-27.

Jallad, R.S. et al. (2005). "Treatment of Acromegaly with Octreotide-LAR: Extensive Experience in a Brazilian Institution," *Clinical Endocrinology* 63(2):168-175.

Jo, Y-H. et al. (Apr. 1, 1998). "Oxytocin Modulates Glutamatergic Synaptic Transmission Between Cultured Neonatal Spinal Cord Dorsal Horn Neurons," *J. Neurosci.* 18(7):2377-2386.

Josey, W.E. et al. (Jul. 15, 1969). "Oxytocin-Induced Water Intoxication," *Am. J. Obstet. Gynecol.* 104(6):926.

Kang, Y.S. et al. (2000). "Brain Uptake and the Analgesic Effect of Oxytocin—its Usefulness as an Analgesic Agent," *Arch. Pharm. Res.* 23(4):391-395.

Kapicioglu, S. et al. (1997). "Treatment of Migraine Attacks with a Long-Acting Somatostatin Analogue (Octreotide, SMS 201-995)," *Cephalalgia* 17(1):27-30.

Kaplan, E. (Jan. 7, 1978). "A Generalized Epileptiform Convulsion After Intra-Amniotic Prostaglandin with Intravenous Oxytocin Infusion: A Case Report," *S. Afr. Med. J.* 53(1):27-29.

Katai, M. et al. (2005). "Octreotide as a Rapid and Effective Painkiller for Metastatic Carcinoid Tumor," *Endocrine Journal* 52(2):277-280.

Kirsch, P. et al. (Dec. 7, 2005). "Oxytocin Modulates Neural Circuitry for Social Cognition and Fear in Humans," *J. Neurosci.* 25(49):11489-11493.

Kitazawa, T. et al. (1998). "Efflux of Taurocholic Acid Across the Blood-Brain Barrier: Interaction with Cyclic Peptides," *The Journal of Pharmacology and Experimental Therapeutics* 286(2):890-895.

Kosfeld, M. et al. (Jun. 2, 2005). "Oxytocin Increases Trust in Humans," *Nature* 435:673-676.

Lamberts, S.W.J. (1988). "The Role of Somatostatin in the Regulation of Anterior Pituitary Hormone Secretion and the Use of Its Analogs in the Treatment of Human Pituitary Tumors," *Endocrine Reviews* 9(4):417-436.

Lamberts, S.W.J. et al. (Jan. 25, 1996). "Octreotide," *The New England Journal of Medicine* 334(4):246-254.

Landgraf, R. (1985). "Plasma Oxytocin Concentrations in Man After Different Routes of Administration of Synthetic Oxytocin," *Exp. Clin. Endocrinol.* 85(2):245-248.

Lee, H.M. et al. (Nov. 28, 2003). "Diclofenac Inhibition of Sodium Currents in Rat Dorsal Root Ganglion Neurons," *Brain Res.* 992(1):120-127.

Lerner, E.N. (Jun. 2004). "Enhanced Delivery of Octreotide to the Brain via Transnasal Iontophoretic Administration," *Journal of Drug Targeting* 12(5):273-280.

Levy, M.J. et al. (Jul./Aug. 2003). "Acromegaly: A Unique Human Headache Model," *Headache* 43(7):794-797.

Levy, M.J. et al. (2003). "Somatostatin Infusion Withdrawal: A Study of Patients with Migraine, Cluster Headache and Healthy Volunteers," *Pain* 102(3):235-241.

Levy, M.J. et al. (2005). "Octreotide is not Effective in the Acute Treatment of Migraine," *Cephalalgia* 25(1):48-55.

Levy, M.J. et al. (Aug. 2005; e-pub. May 11, 2005). "The Clinical Characteristics of Headache in Patients with Pituitary Tumours," *Brain* 128(Pt. 8):1921-1930.

List, M.A. et al. (2000). "Evaluation of Quality of Life in Patients Definitely Treated for Squamous Carcinoma of the Head and Neck," *Curr. Opin. Oncol.* 12:215-220.

Loup, F. et al. (Oct. 23, 1989). "Localization of Oxytocin Binding Sites in the Human Brainstem and Upper Spinal Cord: An Autoradiographic Study," *Brain Res.* 500(1-2):223-230.

Loup, F. et al. (Aug. 2, 1991). "Localization of High-Affinity Binding Sites for Oxytocin and Vasopressin in the Human Brain. An Autoradiographic Study," *Brain Res.* 555(2):220-232.

Lundeberg, T. et al. (Mar. 28, 1994). "Anti-Nociceptive Effects of Oxytocin in Rats and Mice," *Neurosci. Lett.* 170(1):153-157.

Lussier, D. et al. (2004). "Adjuvant Analgesics in Cancer Pain Management," *The Oncologist* 9(5):571-591.

Lustig, R.H. et al. (2006; e-pub. Sep. 13, 2005). "A Multicenter, Randomized, Double-Blind, Placebo-Controlled, Dose-Finding Trial of a Long-Acting Formulation of Octreotide in Promoting Weight Loss in Obese Adults with Insulin Hypersecretion," *International Journal of Obesity* 30(2):331-341.

Lyritis, G.P. et al. (1997). "Pain Relief from Nasal Salmon Calcitonin in Osteoporotic Vertebral Crush Fractures. A Double Blind, Placebo-Controlled Clinical Study," *Acta Orthop. Scand. Suppl.* 275:112-114.

Madrazo, I. et al. (1987). "Intraventricular Somatostatin-14, Arginine Vasopressin, and Oxytocin: Analgesic Effect in a Patient with Intractable Cancer Pain," *Appl. Neurophysiol.* 50(1-6):427-431.

Maeda, Y. et al. (1994). "Inhibitory Effects of Salmon Calcitonin on the Tail-Biting and Scratching Behavior Induced by Substance P and Three Excitatory Amino Acids," *J. Neural Transm. Gen. Sect.* 96(2):125-133.

Matharu, M.S. et al. (Oct. 2004; e-pub. Sep. 30, 2004). "Subcutaneous Octreotide in Cluster Headache: Randomized Placebo-Controlled Double-Blind Crossover Study," *Ann. Neurol.* 56(4):488-494.

Matharu, M.S. et al. (Nov. 2004). "Subcutaneous Octreotide in Cluster Headache: Randomized Placebo-Controlled Double-Blind Crossover Study," Erratum *Ann. Neurol.* 56(5):751.

McKenna, P. et al. (Nov.-Dec. 1979). "Hyponatremic Fits in Oxytocin-Augmented Labors," *Int. J. Gynaecol. Obstet.* 17(3):250-252.

Mens, W.B. et al. (Feb. 28, 1983). "Penetration of Neurohypophyseal Hormones from Plasma into Cerebrospinal Fluid (CSF): Half-Times of Disappearance of These Neuropeptides from CSF," *Brain Res.* 262(1):143-149.

Meunier, A. (Apr. 2005). Attenuation of Pain-Related Behaviours in a Rat Model of Trigeminal Neuropathic Pain by Viral-Driven Enkephalin Overproduction in Trigeminal Ganglion Neurons, *Molecular Therapy* 11(4):608-616.

Millan, M.J. et al. (Sep. 19, 1984). "Vasopressin and Oxytocin in the Rat Spinal Cord: Analysis of Their Role in the Control of Nociception," *Brain Res.* 309(2):384-388.

Miralles, F.S. et al. (Jul. 1987). "Postoperative Analgesia Induced by Subarachnoid Lidocaine Plus Calcitonin," *Anesth. Analg.* 66(7):615-618.

Musolino, N.R. et al. (1990). "Headache in Acromegaly: Dramatic Improvement with the Somatostatin Analogue SMS 201-995," *The Clinical Journal of Pain* 6(3):243-245.

Newman, C.B. et al. (Sep. 1998). "Octreotide as Primary Therapy for Acromegaly," *The Journal of Clinical Endocrinology and Metabolism* 83(9):3034-3040.

Ofluoglu, D. et al. (Jan. 2007). "The Effect of Calcitonin on β-Endorphin Levels in Postmenopausal Osteoporotic Patients with Back Pain," *Clin. Rheumatol.* 26(1):44-49.

Olesen, J. (2004). "The International Classification of Headache Disorders," *Cephalalgia* 24(Suppl. 1):1-151.

Paice, J.A. et al. (Jan. 1996). "Intrathecal Octreotide for Relief of Intractable Nonmalignant Pain: 5-Year Experience with Two Cases," *Neurosurgery* located at <http://gateway.ut.ovid.com/gw1/ovidweb.cgi>, last visited Mar. 30, 2007, ten pages.

Parker, K.J. et al. (Oct. 2005). "Intranasal Oxytocin Administration Attenuates the ACTH Stress Response in Monkeys," *Psychoneuroendocrinology* 30(9):924-929.

Pascual, J. et al. (1991). "Analgesic Effect of Octreotide in Headache Associated with Acromegaly is not Mediated by Opioid Mechanisms. Case Report," *Pain* 47(3):341-344.

Pawlak, M. et al. (2004). "Octreotide, a Somatostatin Analogue, Attenuates Movement Evoked Discharges of Fine Afferent Units from Inflamed Knee Joints of Rats," *Neuroscience Letters* 361(1-3):180-183.

Pedlow, P.R.B. (Dec. 1970). "Syntocinon Induced Convulsion," *J. Obstet. Gynaecol. Br. Commonw.* 77(12):1113-1114.

Penn, R.D. et al. (Apr. 1992). "Octreotide: A Potent New Non-Opiate Analgesic for Intrathecal Infusion," *Pain* 49(1):13-19.

Petersson, M. et al. (Aug. 16, 2005). "Oxytocin Decreases Corticosterone and Nociception and Increases Motor Activity in OVX Rats," *Maturitas* 51(4):426-433.

Petersson, M. et al. (Jul. 12, 1996). "Oxytocin Increases Nociceptive Thresholds in a Long-Term Perspective in Female and Male Rats," *Neurosci. Lett.* 212(2):87-90.

Phillips, W.J. et al. (2006). "Relief of Acute Migraine Headache with Intravenous Oxytocin: Report of Two Cases," *J. Pain Palliat. Care Pharmacother.* 20(3):25-28.

Potter, R.R. (May 1964). "Water Retention Due to Oxytocin," *Obstet Gynecol.* 23:699-702.

Randić, M. et al. (1978). "Depressant Actions of Methionine-Enkephalin and Somatostatin in Cat Dorsal Horn Neurones Activated by Noxious Stimuli," *Brain Res.* 152(1):196-202.

Reiter, M.K. et al. (Jan. 1, 1994). "Localization of Oxytocin Binding Sites in the Thoracic and Upper Lumbar Spinal Cord of the Adult and Postnatal Rat: A Histoautoradiographic Study," *Eur. J. Neurosci.* 6(1):98-104.

Robbins Headache Clinic. (2004). "Combination Therapy for Migraines," located at <http://www.headachedrugs.com/archives2/combination.html>, last visited May 1, 2007, two pages.

Robinson, D.A. et al. (Apr. 15, 2002). "Oxytocin Mediates Stress-Induced Analgesia in Adult Mice," *J. Physiol.* 540(Pt. 2):593-606.

Ross, T.M. et al. (2004). "Intranasal Administration of Interferon Beta Bypasses the Blood-Brain Barrier to Target the Central Nervous System and Cervical Lymph Nodes: A Non-Invasive Treatment Startegy for Multiple Sclerosis," *Journal of Neroimmunology* 151:66-77.

Sahin, F. et al. (Mar. 2006). "Efficacy of Salmon Calcitonin in Complex Regional Pain Syndrome (Type 1) in Addition to Physical Therapy," *Clin. Rheumatol.* 25(2):143-148.

Sakurada, S. et al. (2002). "Recent Advance in the Search for the μ-Opioidergic System: Differential Antinociceptive Effects Induced by Intrathecally-Administered Endomorphin-1 and Endomorphin-2 in Mice," *Jpn. J. Pharmacol.* 89:221-223.

Sances, G. et al. (Apr. 2003). "Course of Migraine During Pregnancy and Postpartum: A Prospective Study," *Cephalalgia* 23(3):197-205.

Sandler, L.M. et al. (1987). "Effective Long-Term Treatment of Acromegaly with a Long-Acting Somatostatin Analogue (SMS 201-995)," *Clinical Endocrinology* 26(1):85-95.

Sayani, A.P. et al. (1996). "Systemic Delivery of Peptides and Proteins Across Absorptive Mucosae," *Critical Reviews in Therapeutic Drug Carrier Systems* 13(1&2):85-184.

Schindler, M. et al. (1997). "Immunohistochemical Localization of the Somatostatin $SST_{2(A)}$ Receptor in the Rat Brain and Spinal Cord," *Neuroscience* 76(1):225-240.

Schindler, M. et al. (1998). "Identification of Somatostatin $sst_{2(a)}$ Receptor Expressing Neurones in Central Regions Involved in Nociception," *Brain Research* 798(1-2):25-35.

Schmidt, K. et al. (May 1993). "Analgesic Effect of the Somatostatin Analogue Octreotide in Two Acromegalic Patients: A Double-Blind Study with Long-Term Follow-up," *Pain* 53(2):223-227.

Schmidt, M. et al. (Jul. 1998). "Somatostatin Receptor Imaging in Intracranial Tumours," *European Journal of Nuclear Medicine* 25(7):675-686.

Schwartz, G. et al. (1996). "Effects of Salmon Calcitonin on Patients with Atypical (Idiopathic) Facial Pain: A Randomized Controlled Trial," *J. Orofac. Pain* 10(4):306-315.

Schwetz, I. et al. (2004). "Anti-Hyperalgesic Effect of Octreotide in Patients with Irritable Bowel Syndrome," *Alimentary Pharmacology & Therapeutics* 19(1):123-131.

Seifer, D.B. et al. (Mar. 1985). "Water Intoxication and Hyponatremic Encephalopathy from the Use of an Oxytocin Nasal Spray," *J. Repro. Med.* 30(3):225-228.

Selmer, I. et al. (2000). "Advances in Understanding Neuronal Somatostatin Receptors," *Regulatory Peptides* 90(1-3):1-18.

Selmer, I-S. et al. (2000). "First Localisation of Somatostatin $sst_4$ Receptor Protein in Selected Human Brain Areas: An Immunohistochemical Study," *Brain Res. Mol. Brain Res.* 82(1-2):114-125.

Sibilia, V. et al. (2000). "Amylin Compared with Calcitonin: Competitive Binding Studies in Rat Brain and Antinociceptive Activity," *Brain Res.* 854(1-2):79-84.

Sicolo, N. et al. (1990). "Analgesic Effect of Sandostatin (SMS 201-995) on Acromegaly Headache," *Minerva Endocrinol.* 15(1):37-42. (Article in Italian, Abstract in English.).

Sicuteri, F. et al. (1984). "Pain Relief by Somatostatin in Attacks of Cluster Headache," *Pain* 18(4):359-365.

Strassman, A.M. et al. (Mar. 2006). "Response Properties of Dural Nociceptors in Relation to Headache," *J. Neurophysiol.* 95(3):1298-1306.

Striebel, H.W. et al. (1996). "Patient-Controlled Intranasal Analgesia: A Method for Noninvasive Postoperative Pain Management," *Anesth. Analg.* 83:548-551.

Szolcsányi, J. et al. (1998). "Release of Somatostatin and Its Role in the Mediation of the Anti-Inflammatory Effect Induced by Antidromic Stimulation of Sensory Fibres of Rat Sciatic Nerve," *British Journal of Pharmacology* 123(5):936-942.

Szolcsányi, J. et al. (1998). "Systemic Anti-Inflammatory Effect Induced by Counter-Irritation Through a Local Release of Somatostatin from Nociceptors," *British Journal of Pharmacology* 125(4):916-922.

Tafazal, S.I. et al. (Feb. 2007). "Randomised Placebo-Controlled Trial on the Effectiveness of Nasal Salmon Calcitonin in the Treatment of Lumbar Spinal Stenosis," *Eur. Spine J.* 16(2):207-212.

Thán, M. et al. (Jul. 7, 2000). "Systemic Anti-Inflammatory Effect of Somatostatin Released from Capsaicin-Sensitive Vagal and Sciatic Sensory Fibres of the Rat and Guinea-Pig," *European Journal of Pharmacology* 399(2-3):251-258.

Thorne, R.G. (2004). "Delivery of Insulin-Like Growth Factor-I to the Rat Brain and Spinal Cord Along Olfactory and Trigeminal Pathways Following Intranasal Administration," *Neuroscience* 127:481-496.

Truini, A. et al. (Sep. 2005). "New Insight into Trigeminal Neuralgia," *J. Headache Pain* 6(4):237-239.

Tsavaris, N. et al. (2006). "Analgesic Activity of High-Dose Intravenous Calcitonin in Cancer Patients with Bone Metastases," *Oncol. Rep.* 16(4):871-875.

Tseng, L.F. (2002). "Recent Advance in the Search for the µ-Opioidergic System: The Antinociceptive Properties of Endomorphin-1 and Endomorphin-2 in the Mouse," *Jpn. J. Pharmacol.* 89:216-220.

Tzabazis, A. et al. (2005). "Differential Activation of Trigeminal C or AδNociceptors by Infrared Diode Laser in Rats: Behavioral Evidence," *Brain Research* 1037:148-156.

Uhl-Bronner, S. et al. (2005). "Sexually Dimorphic Expression of Oxytocin Binding Sites in Forebrain and Spinal Cord of the Rat," *Neuroscience* 135(1):147-154.

Uryvaev,Y.V. et al. (Nov. 1996). "Extremely Low Doses of Oxytocin Reduce Pain Sensitivity in Men," *Bulletin of Experimental Biology and Medicine* 122(5):1071-1073. (Translated from *Byulleten' Eksperimental'noi Biologii i Meditsiny*, 122(11):487-489, Nov. 1996.).

Van Rossum, D. et al. (Sep. 1997). "Neuroanatomical Localization, Pharmacological Characterization and Functions of CGRP, Related Peptides and Their Receptors," *Neurosci. Biobehav. Rev.* 21(5):649-678.

Visser, E.J. et al. (Oct. 2006). "Salmon Calcitonin in the Treatment of Post Herpetic Neuralgia," *Anaesth. Intensive Care* 34(5):668-671.

Wall, G.C. et al. (Apr. 1999). "Calcitonin in Phantom Limb Pain," *Ann. Pharmacother.* 33(4):499-501.

Wang, Y-C. J. et al. (Nov.-Dec. 1980). "Review of Excipients and pH's for Parenteral Products Used in the United States," *J. Parent Drug. Assn.* 34(6):452-462.

Wang, Y-C. J. et al. (1988). "Parenteral Formulations of Proteins and Peptides: Stability and Stabilizers," *J. Parent Sci. and Tech.* 42(2S):S4-S26.

Wang, J-W. et al. (2003). "Antinociceptive Role of Oxytocin in the Nucleus Raphe Magnus of Rats, an Involvement of µ-opioid Receptor," *Regul. Pept.* 115:153-159.

Weeke, J. et al. (1992). "A Randomized Comparison of Intranasal and Injectable Octreotide Administration in Patients With Acromegaly," *The Journal of Clinical Endocrinology and Metabolism* 75(1):163-169.

Wermeling, D.P. et al. (Nov. 4, 2005). "Analgesic Effects of Intranasal Butorphanol Tartrate Administered via a Unit-Dose Device in the Dental Impaction Pain Model: A Randomized, Double-Blind, Placebo-Controlled, Paraleel-Group Study," *Clinical Therapeutics* 27(4):430-440.

Whitfield, M.F. et al. (1980). "Accidental Administration of Syntometrine in Adult Dosage to the Newborn," *Arch. Dis. Child.* 55:68-70.

Wiesenfeld-Hallin, Z. et al. (Sep. 17, 1984). "Subarachnoid Injection of Salmon Calcitonin Does Not Induce Analgesia in Rats," *Eur. J. Pharmacol.* 104(3-4):375-377.

Williams, G. et al. (Oct. 30, 1986). "Improvement in Headache Associated with Prolactinoma During Treatment with a Somatostatin Analogue: an "N of 1" Study," *The New England Journal of Medicine* 315(18):1166-1167.

Williams, G. et al. (Jul. 25, 1987). "Analgesic Effect of Somatostatin Analogue (Octreotide) in Headache Associated with Pituitary Tumours," *British Medical Journal (Clinical Research Ed.)* 295(6592):247-248.

Windle, R.J. et al. (Mar. 24, 2004). "Oxytocin Attenuates Stress-Induced *c-fos* mRNA Expression in Specific Forebrain Regions Associated with Modulation of Hypothalamo-Pituitary-Adrenal Activity," *J. Neurosci.* 24(12):2974-2982.

Witt, D.M. (Jan. 15, 1997). "Regulatory Mechanisms of Oxytocin-Mediated Sociosexual Behavior," *Ann. N.Y. Acad. Sci.* 807:287-301.

Woodhouse, D.R. (Jan. 12, 1980.) "Water Intoxication Associated with High Dose Syntocinon Infusion," *Med. J. Aust.* 1(1):34.

Yang, J. (Apr. 15, 1994). "Intrathecal Administration of Oxytocin Induces Analgesia in Low Back Pain Involving the Endogenous Opiate Peptide System," *Spine* 19(8):867-871.

Young, E.A. (Dec. 2005)."Effects of Estrogen Antagonists and Agonists on the ACTH Response to Restraint Stress in Female Rats," *Neuropsychopharmacology* 25(6):881-891.

Yu, S-Q. et al. (Sep. 5, 2003). "Involvement of Oxytocin in Spinal Antinociception in Rats with Inflammation," *Brain Res.* 983:13-22.

Zadina, J.E. et al. (Apr. 3, 1997). "A Potent and Selective Endogenous Agonist for the µ-Opiate Receptor," *Nature* 386:499-502.

Zubrzycka, M. et al. (Feb. 21, 2005). "Inhibition of Trigemino-Hypoglossal Reflex in Rats by Oxytocin in Mediated by µ and κ Opioid Receptors," *Brain Res.* 1035(1):67-72.

Granger, P. et al. (1995). "Modulation of the γ-Aminobutyric Acid Type A Receptor by the Antiepileptic Drugs Carbamazepine and Phenytoin," *Molecular Pharmacology* 47:1189-1196.

Yang, Q. et al. (2002). "Modulation by Oxytocin of ATP-Activated Currents in Rat Dorsal Root Ganglion Neurons," *Neuropharmacology* 43:910-916.

Final Office Action mailed on Sep. 8, 2009, for U.S. Appl. No. 11/381,383, filed May 3, 2006, 25 pages.

Final Office Action mailed on Jul. 6, 2010, for U.S. Appl. No. 12/409,419, filed Mar. 23, 2009, 9 pages.

Non-Final Office Action mailed on Mar. 21, 2008, for U.S. Appl. No. 11/511,997, filed Aug. 28, 2006, 6 pages.

Non-Final Office Action mailed on Dec. 3, 2009, for U.S. Appl. No. 12/409,419, filed Mar. 23, 2009, 6 pages.

Brown, D.C. et al. (1998). "oxytocin Content of the Cerebrospinal Fluid of Dogs and its Relationship to Pain Induced by Spinal Cord Compression," *Vet. Surg.* 27(6):607-611.

Capsoni, S. et al. (2009). "Delivery of NGF to the Brain: Intranasal Versus Ocular Administration in Anti-NGF Transgenic Mice," *Journal of Alzheimer's Disease* 16:371-388.

Fanciullacci, M. et al. (1997). "Responsiveness of the Trigeminovascular System to Nitroglycerine in Cluster Headache Patients," *Brain* 120:283-288.

Gao, L. et al.(2004). "Involvement of Opioid Receptors in the Oxytocin-Induced Antinociception in the Central Nervous System of Rats," *Regulatory Peptides* 120:53-58.

Non-Final Office Action mailed Dec. 23, 2010, for U.S. Appl. No. 12/409,413, filed Mar. 23, 2009, 8 pages.

Non-Final Office Action mailed on Dec. 27, 2010, for U.S. Appl. No. 11/990,878, filed Aug. 19, 2009, 10 pages.

Non-Final Office Action mailed on Nov. 30, 2011, for U.S. Appl. No. 13/269,527, filed Oct. 7, 2011, 9 pages.

Non-Final Office Action mailed on Dec. 23, 2011, for U.S. Appl. No. 13/165,646, filed Jun. 21, 2011, 17 pages.

Non-Final Office Action mailed on Dec. 23, 2011, for U.S. Appl. No. 12/409,419, filed Mar. 23, 2009, 14 pages.

Non-Final Office Action mailed on Feb. 13, 2012, for U.S. Appl. No. 13/269,527, filed Oct. 7, 2011, 10 pages.

\* cited by examiner

METHODS FOR TREATMENT OF HEADACHES BY ADMINISTRATION OF OXYTOCIN

CROSS-REFERENCE TO RELATED APPLICATIONS

This application is a continuation application of U.S. application Ser. No. 11/511,997, filed Aug. 28, 2006, which claims the benefit of U.S. Provisional Patent Application Ser. No. 60/711,950, filed Aug. 26, 2005 and U.S. Provisional Patent Application Ser. No. 60/794,004, filed Apr. 21, 2006, the entire contents of which are hereby incorporated by reference herein in their entirety.

TECHNICAL FIELD

The present invention relates generally to methods and compositions for the treatment of headache and headache or head pain disorders. More specifically, the present invention relates to methods for the treatment or prevention of primary or secondary headaches by administration of oxytocin. In particular, the present invention relates to methods for the treatment or prevention of migraine, cluster, tension headaches or trigeminal neuralgia by administration of oxytocin or pharmaceutical compositions comprising oxytocin to individuals in need of treatment.

BACKGROUND OF THE INVENTION

Although the epidemiology of headache disorders is only partly documented, taken together, headache disorders are extraordinarily common. It has been estimated that worldwide approximately 240 million people have migraine attacks each year. The National Headache Foundation states that more than 29.5 million Americans suffer from migraine headaches, with women being affected three times more often than men. In addition, in developed countries, tension type or "stress" headaches are estimated to affect two-thirds of all adult males and over 80% of adult females. Less well known is the prevalence of chronic daily headaches although the World Health Organization (WHO) estimates that one adult in 20 has a headache every or nearly every day. Trigeminal neuralgia is not a common disorder but the pain associated with trigeminal neuralgia attacks has been described as among the most severe known to mankind.

Not only are headaches painful, but headache disorders can be disabling to afflicted individuals. Worldwide, according to the WHO, when analyzing all causes for "years lived with disability" migraine headaches were rated 19th on the list. Headache disorders may impose substantial hardships and burdens on the afflicted individuals including personal suffering, impaired quality of life and high financial cost. Repeated headache attacks, and often the constant fear of the next one, can damage an individual's family life, social life and their productivity at their place of employment. For example, it is estimated that social activity and work capacity are reduced in almost all migraine sufferers and in 60% of tension headache sufferers. Finally, the long-term effort of coping with a chronic headache disorder may also predispose an individual to other illnesses. For example, depression is three times more common in people with migraine or severe headaches than in healthy individuals.

A wide range of headache types have been classified by the International Headache Society and among them are primary types including vascular, trigemino-autonomic and tension headaches and secondary types including headaches resulting from infection, trauma and non-vascular, intracranial disorders.

Vascular headaches refer to a group of headache conditions in which events at the interface between meningeal blood vessels and afferent nerve fibers are critical major components in the production of pain. Afferent nociceptive nerve fibers innervating meningeal blood vessels become activated in response to inflammatory and related events at the perivascular sheet causing a throbbing or pulsating type of pain. The most common type of vascular headache is migraine. Current pathophysiological evidence suggests that the trigemino-vascular system plays a pivotal role in the genesis of migraine headache. Migraine headache characteristics include unilateral (60%) or bilateral head pain, pain with a pulsating or throbbing quality, moderate to severe pain, pain associated with nausea or vomiting, sensitivity to light and sound, attacks that last four to 72 hours (sometimes longer) and visual disturbances or aura. Physical exertion often makes a migraine headache worse and women are more likely than men to have migraine headaches. Approximately one to two-fifths of migraine sufferers experience an aura, a sensory phenomena including visual disturbances that precede the onset of migraine headache. It is now believed that the aura is due to transient changes in the activity of specific nerve cells.

Another type of primary vascular headache is "cluster" headache, which is diagnosed by a well characterized clinical presentation. Although the syndrome is well defined from a clinical point of view, the causes are not well understood. The pathophysiology is believed to be associated with the trigemino-autonomic system. The periods during which cluster headache is experienced can last several weeks or months and then disappear completely for months or years leaving pain-free intervals between headache series. Cluster headache is characterized by frequent attacks of short lasting (15-180 minutes), severe, uniform, unilateral head pain associated with autonomic symptoms (e.g. lacrimation and nasal congestion). Pain can occur on the opposite side when a new series starts, pain may be localized behind the eye or in the eye region and may radiate to the forehead, temple, nose, cheek or upper gum on the affected side. Pain is generally extremely intense and severe and often described as a burning, boring, stabbing or piercing sensation. The headaches occur regularly, generally at the same time each day. Many individuals get one to four headaches per a day during a cluster period. Cluster headache is less common than migraine or tension headache and its cause is unknown. In contrast to migraine headaches, cluster headaches occur more in men than women and individuals suffering from these attacks may be very restless.

Tension headache, often referred to as "stress" headache, is a non-specific type of primary headache, which is of non-vascular origin and rarely is related to an organic disease. The pathophysiology of tension headaches is thought to involve the myo-facial system. For example, tension headache may be caused by the tightening of facial and neck muscles, clenching or grinding of teeth and/or poor posture. Tension headaches can be episodic and chronic in course, and typically are of mild to moderate intensity. Verbal descriptor used to characterize tension headache include pressing, dull aching and/or non-pulsating. Tension head pain is typically bilateral, and is not aggravated by physical activity.

Trigeminal neuralgia, also called "tic duloreaux" is a condition that affects the trigeminal nerves and results in severe facial and head pain. Trigeminal neuralgia most commonly is diagnosed in patients over age 50, is slightly more common in women and has an incidence of approximately 4-5 per 100, 000 persons. Trigeminal neuralgia is characterized by sudden severe, sharp facial pain, which usually starts without warning. The quick bursts of pain are described as "lightening bolt-like", "machine gun-like" or "electric shock-like". The pain is generally on one side of the face and is spasmodic, coming in short bursts lasting a few seconds which may repeat many times over the course of a day. Trigeminal neuralgia can involve one or more branches of the trigeminal nerve and the causes are not well characterized.

Current Treatments

There are numerous treatment strategies for migraine and associated symptoms (e.g. nausea). However, to date, there is no single treatment strategy (including prevention or prophylaxis) that successfully alleviates migraine in a majority of patients. Additionally, treatment that has proven effective in one particular migraine sufferer may only be partially or intermittently effective. The current standard of care for migraine focuses on three major areas: 1) acute or abortive treatment; 2) treatment to relieve specific symptoms; and 3) preventive treatment.

Abortive treatment is always indicated because of the disabling nature of migraine attacks. Sumitriptan and related 5-hydroxytryptamine (5-HT-1, serotonin) receptor agonists (triptans) are often considered the therapy of choice for migraine headache. To show optimal effectiveness, these agents generally have to be given early in the onset of pain. Serotonin receptor agonists are effective in up to 70% of patients and generally have few side effects when used sporadically. The number of patients benefiting from treatment with triptans may decrease to less than 50% during long-term therapy. Despite being effective, serotonin receptor agonists often only partially attenuate migraine headache. Rebound pain frequently occurs during the time period during which the drug levels are falling. Furthermore, side effects may arise including dizziness, heaviness or pressure on the chest and arms, shortness of breath, and sometimes chest pain which limit their clinical utility. Triptans are contra-indicated for patients with coronary artery disease. Other members of this class of drugs include, but are not limited to, sumatriptan, zolmitriptan, naratriptan, rizatriptan and elitriptan. Other classes of drugs that are used to treat migraine include the nonsteroidal anti-inflammatory drugs (NSAIDs), ergotamines and on occasion, neuroleptic drugs such as compazine. NSAIDS are as effective as triptans in alleviating migraine headache when given at the onset of mild migraine headache. Ergotamines, although commonly prescribed, are less effective than triptans and NSAIDS. Opioids such as codeine and butorphanol are not a first choice for the treatment of migraine because of their limited effectiveness, associated side effects including sedation and respiratory depression and the potential for dependence and abuse.

Preventive treatment strategies are considered whenever migraine attacks have occurred several times in a month or are very severe and do not respond well to abortive medication. The following classes of drugs are used for preventing migraine: beta-blockers (e.g. propranolol, metoprolol, atenolol), calcium channel blockers, NSAIDs, antidepressants, anti-convulsant drugs (e.g. divalproex sodium, topiramate) and methysergide (no longer available in the United States). Another avenue for preventive treatment is educating the migraine patient to recognize and avoid migraine triggers which may help to reduce the frequency of attacks. Common migraine triggers include, but are not limited to, weather changes, bright lights, strong odors, stress and foods.

In a significant number of patients abortive and preventive treatments for migraine headache are often either ineffective, only partially effective or associated with significant side effects including hypotension, tiredness, increased weight, breathlessness, dizziness, heaviness or pressure on the chest and arms, shortness of breath, chest pain, nausea, muscle cramps, or peripheral vasoconstriction.

Treatment strategies for cluster headache are classified as abortive or preventive. Abortive treatments are directed at stopping or reducing the severity of an attack, while preventive treatments are used to reduce the frequency and intensity of individual headache bouts. Abortive treatment strategies of cluster headache are quite successful when drugs can be injected. Drug classes used for injection include the 5HT1-agonists (e.g. sumatriptan) and the ergotamines. Alternatively, inhalation of 100% oxygen or an occipital nerve block have proven effective. However, all these treatment strategies require a visit to a doctor's office or to an emergency room.

Because of the short-lived nature of cluster headaches, preventive therapy is the cornerstone for individuals who have frequent attacks which severely affect their quality of life. Preventive therapy is initiated at the start of a cluster headache cycle and continues until the person is free of headaches for at least 2 weeks. The dosage of the preventive drug is then slowly tapered off which helps prevent relapsing headaches. Drug classes used preventively include beta-blockers, tricyclic antidepressants, anti-convulsants (e.g., divalproex sodium, topiramate), calcium channel blockers (e.g., verapamil), cyproheptadine, and NSAIDs (e.g. naproxen). Unlike drugs that ablate cluster headache (abortive drugs), most of the drugs used to prevent cluster headache have been developed for other clinical conditions and unfortunately, their effectiveness in prevention is limited.

Treatment for tension headache usually consists of nonprescription painkillers such as aspirin, acetaminophen, NSAIDs or combinations of these agents with caffeine or sedating medications. When severe muscle contraction is present and/or the tension headache becomes chronic, more powerful prescription drugs may be needed to achieve relief. Tricyclic anti-depressants including amitriptyline HCl, doxepin HCl and nortriptyline HCl are commonly used. However these drugs have significant side effects including sedation, weight gain, dry mouth and constipation.

The first line treatment of trigeminal neuralgia is pharmacological in nature and is based on the use of antiepileptic agents including gabapentin, baclofen, clonazepam, lamotrigine, oxcarbazepine, toprimate and carbamazepine. About 50% of patients initially respond to treatment with a single agent and about 70% respond to treatment with two agents. However, a significant portion of patients (>50%) eventually becomes refractory to drug treatment and adding of a third agent or an analgesic drug (opioid or a non-steroidal anti-inflammatory agent) does not improve therapeutic success. Therapy with antiepileptic agents is also associated with side effects, most prominently dizziness, drowsiness, and ataxia. Many antiepileptic agents have the potential to cause rare but serious reactions.

Considering surgical interventions is the next appropriate step in patients who are refractory to pharmacological interventions. Surgical techniques include radio-frequency ablation of the trigeminal ganglion, micro-vascular decompression of the trigeminal root and gamma-knife radiation to the trigeminal root. The success rate of surgical techniques is initially quite high (80-90%) while the longer term success is closer to 50%. Specific side effects of these surgical interventions are sensory loss (numbness) and/or dysesthesia (e.g. analgesia dolorosa) in the distribution of the trigeminal nerve. Micro-vascular decompression in particular can be complicated by the occurrence of meningitis, cerebrospinal fluid leaks, or cranial nerve deficits. This procedure requires a craniotomy and the published mortality rate for this procedure is significant at 0.2-1.2%.

It is clear that migraine, cluster and tension headaches as well as trigeminal neuralgia can be debilitating to individuals and significantly impair their quality of life. To date, there does not appear to be a class of drugs or a treatment regimen that is effective for a majority of patients suffering from primary or secondary headaches or suffering from trigeminal neuralgia. Therefore, there is still a great need for novel and more effective therapies preventing or alleviating head pain of any origin.

BRIEF SUMMARY OF THE INVENTION

Provided herein are methods for the treatment of headache or trigeminal neuralgia comprising administering to an individual an effective amount of an oxytocin peptide. Some aspects of the invention include methods wherein the oxytocin peptide is administered in combination with at least one additional analgesic agent. Some aspects of the invention include methods wherein the administration results predominantly in analgesia to the facial or head region, as compared to analgesic effects in other parts of the body, and in alleviation of the headache pain. Some aspects of the invention include methods wherein the headache pain is a result of a primary headache or a secondary headache. In some examples the primary headache is a vascular headache or a tension-type headache. In some examples the vascular headache is a migraine or a cluster type headache. In some examples the secondary headache results from an infection, ingestion of toxin, or over-consumption of alcohol. Other aspects of the invention include methods wherein the head pain is a result of trigeminal neuralgia.

Provided herein are methods for the treatment of headache or trigeminal neuralgia pain in an individual, comprising administering to the individual an effective amount of an oxytocin peptide. In some aspects of the invention, the oxytocin peptide is administered via mucosal administration. In some examples the oxytocin peptide is administered intranasally. In other examples the oxytocin peptide is administered via buccal or sublingual administration. In other examples the oxytocin peptide is administered to conjunctiva or other mucosal tissues around the eye. In some aspects of the invention, the oxytocin peptide is administered via transdermal administration. In some examples the oxytocin peptide is administered to the skin or dermal surface. In other examples the oxytocin peptide is administered to the skin by intradermal or subcutaneous injection. In some examples the oxytocin peptide is targeted to the trigeminal nerve system and results predominantly in analgesia to the facial or head region.

Some aspects of the invention include methods for prevention of headache pain or trigeminal neuralgia comprising administering to an individual in need thereof an effective dose of an oxytocin peptide. In some aspects of the present invention, the methods comprise prophylactic treatment for migraine-associated pain comprising administering an oxytocin peptide to an individual experiencing a migraine-associated aura prior to onset of a migraine headache. In some aspects of the present invention, the methods comprise prophylactic treatment for cluster headache pain comprising administering an oxytocin peptide to an individual after a cluster series has started but prior to successive headaches in the cluster series. In some aspects of the present invention, the methods comprise prophylactic treatment for trigeminal neuralgia pain comprising administering an oxytocin peptide to an individual after a trigeminal neuralgia attack but prior to successive attacks.

Some aspects of the invention include methods wherein an oxytocin peptide is administered as a pharmaceutical composition. Accordingly, provided herein are methods for treatment and/or prevention of headache pain or trigeminal neuralgia in an individual, comprising: administering to the individual an effective amount of a pharmaceutical composition comprising an oxytocin peptide wherein the oxytocin peptide is administered via intravenous injection, subcutaneous injection, mucosal or transdermal administration. Some aspects of the invention include methods wherein the pharmaceutical composition further comprises at least one additional analgesic agent. Some aspects of the invention include methods wherein the pharmaceutical composition is administered in a formulation selected from a group comprising a powder, a liquid, a gel, a film, an ointment, a suspension, a cream or a bioadhesive. Some aspects of the invention include methods wherein the pharmaceutical composition further comprises a protease inhibitor, an absorption enhancer, a vasoconstrictor or combinations thereof. In some examples, the protease inhibitor is selected from a group comprising antipain, arphamenine A and B, benzamidine HCl, AEBSF, CA-074, calpain inhibitor I and II, calpeptin, pepstatin A, actinonin, amastatin, bestatin, chloroacetyl-HOLeu-Ala-Gly-$NH_2$, DAPT, diprotin A and B, ebelactone A and B, foroxymithine, leupeptin, pepstatin A, phosphoramidon, aprotinin, BBI, soybean trypsin inhibitor, phenylmethylsulfonyl fluoride, E-64, chymostatin, 1,10-phenanthroline, EDTA and EGTA. In some examples the absorption enhancer is selected from a group comprising surfactants, bile salts and analogues thereof (e.g. sodium taurodihydrofusidate), bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

Provided herein are methods for treatment and/or prevention of headache pain or trigeminal neuralgia in an individual comprising administering to the individual i) an effective amount of a pharmaceutical composition comprising an oxytocin peptide and ii) a vasoconstrictor. Generally, administration of the vasoconstrictor reduces systemic distribution of the oxytocin peptide. In some examples the vasoconstrictor is selected from the group comprising phenylephrine hydrochloride, tetrahydrozoline hydrochloride, naphazoline nitrate, oxymetazoline hydrochloride, tramazoline hydrochloride, ergotamine, dihydroergotamine, endothelin-1, endothelin-2, epinephrine, norepinephrine and angiotensin. In some examples the vasoconstrictor is administered prior to the administration of the pharmaceutical composition. In other examples the vasoconstrictor is co-administered with the pharmaceutical composition. In some examples administration of the vasoconstrictor results in a decreased effective dosage requirement of the oxytocin peptide. In other examples the pharmaceutical composition further comprises at least one additional analgesic agent.

Provided herein are methods for treatment and/or prevention of headache pain or trigeminal neuralgia in an individual comprising administering to the individual an effective amount of a pharmaceutical composition comprising an oxytocin peptide. In some examples, the oxytocin peptide is administered via buccal or sublingual administration. In other examples, the pharmaceutical composition is administered by intranasal administration. In some examples, the pharmaceutical composition is administered by intranasal administration to the nasal cavity. In one example the intranasal administration is directed to the inferior two-thirds of the nasal cavity. In another example the administration is directed to the inferior region of the nasal cavity, thus directing it away from the nasal mucosal region innervated by the olfactory nerve. In some examples the pharmaceutical composition is administered by transdermal, intradermal or subcutaneous administration to the skin or dermal surface.

Provided herein are methods for treatment and/or prevention of headache pain or trigeminal neuralgia in an individual comprising administering to the individual an effective amount of an oxytocin peptide or a pharmaceutical composition comprising an oxytocin peptide in combination with an additional active agent. In some examples the pharmaceutical composition further comprises at least one additional active agent. In other examples the pharmaceutical composition further comprises at least two additional active agents. In some examples the additional active agent is selected from the group consisting of non-peptide opioids, opioid and opioid-like peptides and their analogs, NMDA-receptor antagonists, sodium channel blockers, calcium channel blockers, adrenergic antagonists, gabaergic agonists, glycine agonists, cholinergic agonists, adrenergic agonists, such as epinephrine, anticonvulsants, Rho kinase inhibitors, PKC inhibitors, p38-MAP kinase inhibitors, ATP receptor blockers, endothelin receptor blockers, pro-inflammatory cytokine blockers, pro-inflammatory chemokine blockers, pro-inflammatory interleukin blockers and tumor necrosis factor blockers, anti-inflammatory cytokines, tricyclic antidepressants, serotonergic antagonists, serotonergic agonists, NSAIDs and COXIBs, acetaminophen; analgesic peptides, toxins, TRP channel agonists and antagonists, cannabanoids, antagonists of pro-nociceptive peptide neurotransmitter receptors CGRP1 and CGRP2, antagonists of pro-nociceptive peptide neurotransmitter receptor NK1, antagonists of pro-nociceptive peptide neurotransmitter receptor NK2, antagonists of pro-nociceptive peptide neurotransmitter receptor Y1-5, antagonists of pro-nociceptive peptide neurotransmitter receptors VPAC2, VPAC1 and PAC1, antagonists of pro-nociceptive peptide neurotransmitter receptor receptors Gal1-3 and GaiR1-3, agonists or antagonists of vasopressin, corticotropin releasing hormone (CRH), growth hormone releasing hormone (GHRH), luteinizing hormone releasing hormone (LHRH), somatostatin growth hormone release inhibiting hormone, thyrotropin releasing hormone (TRH), glial-derived neurotrophic factor (GDNF), brain-derived neurotrophic factor (BDNF), nerve growth factor (NGF), neurotrophin-3 (NT-3), pancreatic polypeptide, peptide tyrosine-tyrosine, glucogen-like peptide-1 (GLP-1), peptide histidine isoleucine (PHI), pituitary adenylate cyclase activating peptide (PACAP), brain natriuretic peptide, cholecystokinin (CCK), islet amyloid polypeptide (IAPP) or amylin, melanin concentrating hormone (MCH), melanocortins (ACTH, α-MSH and others), neuropeptide FF (F8Fa), neurotensin, parathyroid hormone related protein, calcitonin, Agouti gene-related protein (AGRP), cocaine and amphetamine regulated transcript (CART)/peptide, 5-HT-moduline, hypocretins/orexins, nociceptin/orphanin FQ, ocistatin, prolactin releasing peptide, secretoneurin, urocortin and derivatives and analogues thereof. In some examples the additional active agent is diclofenac.

Provided herein are methods for treatment and/or prevention of headache pain or trigeminal neuralgia in an individual comprising administering to the individual an effective amount of an oxytocin peptide or a pharmaceutical composition comprising an oxytocin peptide. In some examples, administration of an oxytocin peptide or a composition comprising an oxytocin peptide results in reduction of a pain rating on the VAS of 30% or more. In other examples, administration of an oxytocin peptide or a composition comprising an oxytocin peptide results in reduction of a pain rating on the VAS of 50% or more.

Provided are kits for carrying out any of the methods described herein. Kits are provided for use in treatment and/or prevention of headache pain and headache disorders. Kits of the invention comprise an oxytocin peptide in suitable packaging. Some kits may further comprise at least one additional analgesic agent. Some kits may further comprise a vasoconstrictor, at least one protease inhibitor, and/or at least one absorption enhancer. Some kits may further comprise a delivery device, including but not limited to, a device for intranasal administration. The kits may further comprise instructions providing information to the user and/or health care provider for carrying out any of the methods described herein.

BRIEF DESCRIPTION OF THE DRAWINGS

FIG. 3A shows responses (action potentials per 30 stimuli) to repeated stimulation of a rat's face before and after oxytocin administration. FIG. 3B shows the approximate site (black spot) of administration on the rat's face of the electrical administration. FIG. 3C shows raw data recorded during electrical stimulation before oxytocin administration. FIG. 3D. shows raw data recorded during electrical stimulation 30 minutes after intranasal oxytocin administration.

DETAILED DESCRIPTION OF THE INVENTION

Definitions

Figure 1:
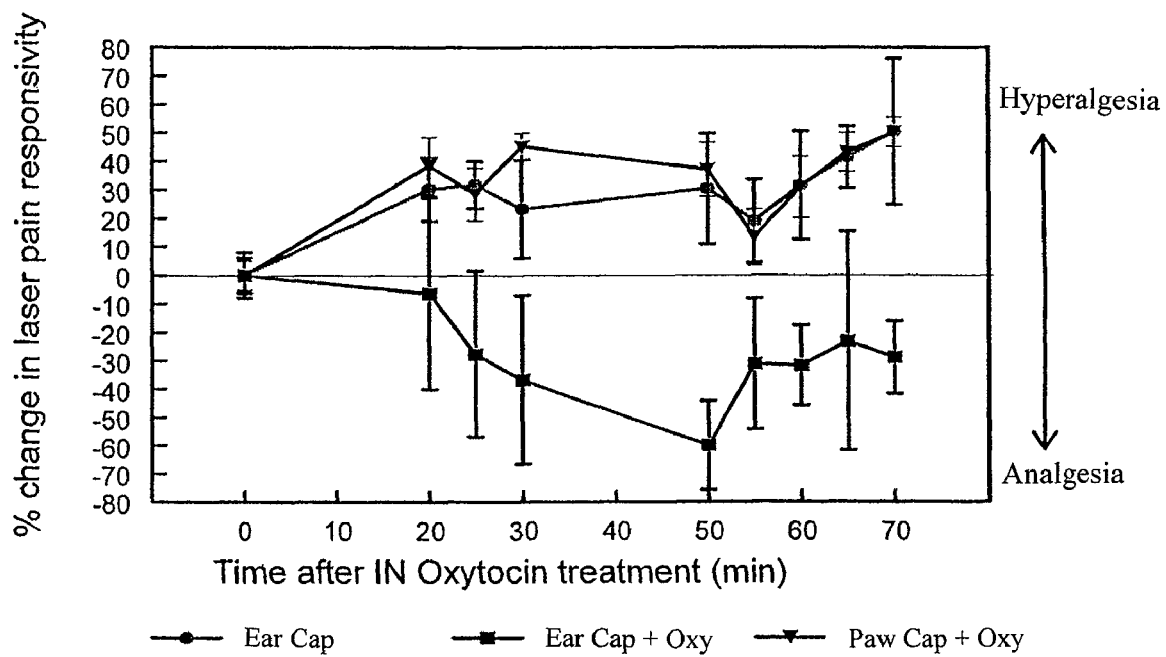
FIG. 1 depicts data demonstrating withdrawal latencies after noxious thermal stimulation to the ears or hindpaws in a rat model after intranasal administration of oxytocin. Rats were intranasally administered 10 μg oxytocin and withdrawal latencies were tested. Each data point represents the average, across 8 animals, of latencies in response to stimulation at a particular time after the beginning of the test. The circles represent the withdrawal latencies after thermal stimulation to the ear in control rats treated with saline. The squares represent the withdrawal latencies after thermal stimulation to the ear in rats treated with 10 μg oxytocin. The triangles represent the withdrawal latencies after thermal stimulation to the hindpaw in the treated rats.

As used herein, unless otherwise specified, the term "treatment" or "treating pain" refers to administration to an individual of an agent of interest wherein the agent alleviates or prevents a pathology for which the individual is being treated. "Treatment for headache pain", "treatment of headache" or "treatment of head pain" refers to the alleviation or prevention of pain associated with headache disorders and trigeminal neuralgia.

As used herein, unless otherwise specified, the term "prevention", "prophylaxis" or "preventing pain" refers to administration to an individual of an agent of interest wherein the agent alleviates or prevents a pathology for which the individual is being treated. "Prevention of headache pain", "prevention of headache" or "prevention of head pain" refers to the alleviation or prevention of pain associated with headache disorders and trigeminal neuralgia.

As used herein, "central nervous system" or "CNS" refers to that part of the nervous system that is embedded in cerebrospinal fluid (CSF) including the brain, the spinal cord and proximal aspects of peripheral nerves entering the space embedded in CSF. The CNS is one of the two major divisions of the nervous system. The other is the peripheral nervous system which is outside of the brain and spinal cord and includes the peripheral portions of the cranial nerves—of which the trigeminal nerve is a member.

Although analgesia in the strictest sense is an absence of pain, as used herein, "analgesia" refers to reduction in the intensity of the pain perceived by an individual without causing general numbness.

As used herein, "analgesia agent", "analgesic agent" or "analgesic" refers to any biomolecule, drug or active agent that alleviates or prevents pain.

As used herein, "oxytocin" or "oxytocin peptide" refers to a substance having biological activity associated with natural oxytocin. Oxytocin or oxytocin peptide can be a naturally occurring endogenous peptide, fragments, analogues or derivatives thereof. Oxytocin or oxytocin peptide can also be a non-endogenous peptide, fragments, analogues or derivatives thereof.

As used herein, "analogues and derivatives" refers to any peptide analogous to naturally occurring oxytocin wherein one or more amino acids within the peptide have been substituted, deleted, or inserted. The term also refers to any peptide wherein one or more amino acids have been modified, for example by chemical modification. In general, the term covers all peptides which exhibit oxytocin activity but which may, if desired, have a different potency or pharmacological profile.

As used herein, "migraine" includes migraine headache, migraine without aura, migraine with aura, and migraine with aura but without headache.

As used herein, "cluster headache" includes cluster headache, cluster-type headache, histamine headache, histamine cephalalgia, Raedar's syndrome, and sphenopalatine neuralgia.

As used herein, "tension headache" includes tension headache, tension-type headache, muscle contraction headache and stress headache.

As used herein, "headache disorder" includes migraine, tension headache, cluster headache, trigeminal neuralgia, secondary headaches, and miscellaneous-type headache.

As used herein, "pain" includes acute pain, chronic pain and episodic pain.

As used herein "systemic side effects" include, but are not limited to, cardiovascular including peripheral vasodilation, reduced peripheral resistance, and inhibition of baroreceptors; dermatologic including pruritus (itching), flushing and red eyes; gastrointestinal including nausea and vomiting, decreased gastric motility in stomach, decreased biliary, pancreatic and intestinal secretions and delays in food digestion in small intestine, diminished peristaltic waves in large intestine contributing to constipation, epigastric distress or biliary colic in biliary tract; respiratory including depressed respiratory rate; and urinary including urinary urgency and difficulty with urination, and peripheral limb heaviness.

As used herein, "central nervous system effects" or "CNS effects" include, but are not limited to, narcosis, euphoria, drowsiness, apathy, psychotic ideation, mental confusion, alteration in mood, reduction in body temperature, feelings of relaxation, dysphoria (an emotional state characterized by anxiety, depression, or unease), nausea and vomiting (caused by direct stimulation of chemoreceptors in the medulla).

As used herein, "mucosal administration" or "administered transmucosally" refers to delivery to the mucosal surfaces of the nose, nasal passageways, nasal cavity; the mucosal surfaces of the oral cavity including the gingiva (gums), the floor of the oral cavity, the cheeks, the lips, the tongue, the teeth; and the mucosal surfaces of or around the eye including the conjunctiva, the lacrimal gland, the nasolacrimal ducts, the mucosa of the upper or lower eyelid and the eye.

As used herein, "intranasal administration" or "administered intranasally" refers to delivery to the nose, nasal passageways or nasal cavity by spray, drops, powder, gel, film, inhalant or other means.

The nasal cavity contains turbinate bones which protrude into the nasal cavity and generally separate it into three regions. As used herein, the "inferior region of the nasal cavity" refers to the portion of the nasal cavity where the middle and inferior turbinate bones protrude and is a region of the nasal cavity that is innervated by the trigeminal nerve system. The superior area of the nasal cavity is defined by the superior turbinate bone wherein the olfactory region is located.

As used herein, "transdermal administration" or "dermal administration" refers to delivery to the skin including the face, neck, scalp, body or combinations thereof. As used herein, dermal administration can include intradermal or subcutaneous administration by various means such as an injection.

As used herein, "pharmaceutically acceptable carrier" or "suitable carrier" refers to a carrier that is conventionally used in the art to facilitate the storage, administration, and/or the healing effect of the agent.

As used herein, "therapeutically effective dose", "therapeutically effective amount" or "an effective amount" refers to an amount of an analgesic agent that is useful for treating pain.

As used herein, "prophylactically effective dose", "prophylactically effective amount" or "an effective amount" refers to an amount of an analgesic agent that is useful for preventing pain.

As used herein, "visual analogue scale" or "VAS" refers to a commonly used scale in pain assessment. It is a 10 cm horizontal or vertical line with word anchors at each end, such as "no pain" and "worst pain imaginable". A subject or patient is asked to make a mark on the line to represent pain intensity. This mark is converted to distance in either centimeters or millimeters from the "no pain" anchor to give a pain score that can range from 0-10 cm or 0-100 mm. The VAS may refer to an 11 point numerical pain rating scale wherein 0 equals "no pain" and 10 equals the "worst pain imaginable".

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

Active Agents

Oxytocin was one of the first peptide hormones to be isolated and sequenced. It is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO:1). Oxytocin is released from the posterior lobe of the pituitary gland and stimulates the contraction of smooth muscle of the uterus during labor and facilitates release of milk from the breast during nursing. Studies have shown that oxytocin may exert a wide spectrum of other biological effects including control of memory and learning processes, and various types of maternal and sexual behavior. In addition, oxytocin may participate in the control of cardiovascular functions, thermoregulation and fluid balance. Other studies have shown that oxytocin can play an important role in nociceptive modulation. Oxytocin is approved by the Food and Drug Administration for intravenous use to induce labor in pregnant women as well as for the treatment of postpartum hemorrhage. Oxytocin has not been previously used for treatment and/or prevention of headache or headache disorders.

The oxytocin peptide for use in the methods described herein can be natural or synthetic, therapeutically or prophylactically active, peptide fragments, peptide analogues, and chemically modified derivatives or salts of active peptides. There are processes described for the production of oxytocin, see for example U.S. Pat. Nos. 2,938,891 and 3,076,797; in addition, oxytocin is commercially available. A variety of peptide analogues and derivatives are available and others can be contemplated for use within the invention and can be produced and tested for biological activity according to known methods. Oxytocin analogues may included, but are not limited to, 4-threonine-1-hydroxy-deaminooxytocin, 4-serine, 8-isoleucine-oxytocin, 9-deamidooxytocin, 7-D-proline-oxytocin and its deamino analog, (2,4-diisoleucine)-oxytocin, deamino oxytocin analog, 1-deamino-1-mono-carba-E12-Tyr(OMe)]-OT(dCOMOT), carbetocin, 4-threonine, 7-glycine-oxytocin (TG-OT), oxypressin, deamino-6-carba-oxytoxin (dC60), L-371,257 and the related series of compounds containing an ortho-trigluoro-ethoxyphenylacetyl core such as L-374,943. Peptides for use within the invention can be peptides that are obtainable by partial substitution, addition, or deletion of amino acids within a naturally occurring or native peptide sequence. Peptides can be chemically modified, for example, by amidation of the carboxyl terminus (—NH$_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide.

All peptides described and/or contemplated herein can be prepared by chemical synthesis using either automated or manual solid phase synthetic technologies, generally known in the art. The peptides can also be prepared using molecular recombinant techniques known in the art.

In some aspects of the invention, an oxytocin peptide is administered in combination with at least one additional active agent. Additional active agents may include, but are not limited to, non-peptide opioids, such as morphine, methadone, fentanyl, butorphanol, codeine, opium, oxycodone, loperimide, meperidine (Demerol), diphenoxylate, propoxyphene (Darvon), 4-methyl fentanyl, hydrocodone, morphine, diacetylmorphine, dihydrocodeine, hydromorphone (Dilaudid), levorphanol (Levo-Dromoran), dextromethorphan, oxymorphone (Numorphan), heroin, remifentanil, phenazocine, pentazocine, piminodine, anileridine, buprenorphine (Suboxone), sufentanil, carfentanil, alfentanil and the atypical opiates, tramadol and tapentadol; opioid and opioid-like peptides and their analogs, such as endorphins, enkephalins, dynorphins, dermorphins, dermenkephalins, morphiceptin, endomorphins and dalargin; NMDA-receptor antagonists, such as ketamine, amantadine, dextrometorphane, memantine and MK801; sodium channel blockers, such as local anesthetics and ergotamine; calcium channel blockers, such as verapamil and nifedipine; adrenergic antagonists, such as propranolol, metoprolol and yohimine; gabaergic agonists, such as GABA, baclofen, cis-4-aminocrotonic acid (CACA), trans-4-aminocrotonic acid (TACA), CGP 27 492 (3-aminopropyl phosphonous acid) and progabide; glycine agonists, such as glycine and D-cycloserine; cholinergic agonists, such as neostigmine and physiostigmine; adrenergic agonists, such as epinephrine, neosynephrine, clonidine and dexmedetomidine; anticonvulsants, such as gabapentin and barbiturates; Rho kinase inhibitors, such as fasudil, Y27632, H-1152 and derivatives thereof; PKC inhibitors, such as chelerythrine, Gö 6983, Gö 6976, N-myristoyl-Ser-Ile-Tyr-Arg-Arg-Gly-Ala-Arg-Arg-Trp-Arg-Lys-Leu, Rottlerin, KAI-9803 and KAI-1455; p38-MAP kinase inhibitors, such as SCIO-469, AMG548 and derivatives thereof; ATP receptor blockers, such as tetramethylpyrazine chelerythrine chloride, A-317491 and derivatives thereof; endothelin receptor blockers, such as BQ123, BMS182874 and derivatives thereof; pro-inflammatory cytokine, chemokine, interleukin and tumor necrosis factor blockers, such as anakinra, infliximab, etanercept and adalimumab; anti-inflammatory cytokines, such as interleukin-4, interleukin-10 and interleukin-13; tricyclic antidepressants, such as desipirmine and amitryptiline; serotonergic antagonists, such as fluoxetine, dolasetron and ondansetron; serotonergic agonists, such as buspirone and ergometrine; NSAIDs and COXIBs, such as diclofenac, ibuprofen, ketorolac, salicylate, rofecoxib, celecoxib, parecoxib, valdecoxib and naproxen; acetaminophen; analgesic peptides, such as calcitonin, octreotide, somatostatin, vasopressin, galanin, the C-fragment of lipotropin and Ac-rfwink-NH$_2$; toxins, such as botulinum toxin, variants and derivatives thereof, cone snail toxins, such as omega-conotoxin GV1A, omega-conotoxin MVIIA, saxitoxin and tetrodotoxin; TRP channel agonists and antagonists, such as capsaicin, capsazepine, resiniferotoxin, SB-705498, A-425619, AMG 517, SC0030 and derivatives thereof; cannabanoids, such as THC, CT-3, levonantradol, dexanabinol, WIN-55, 212-2, AM 1241, dronabinol, nabilone, cannabis medicinal extract (CME) and derivatives thereof; antagonists of pro-nociceptive peptide neurotransmitter receptors CGRP1 and CGRP2, including non-peptide antagonists such as BIBN4096 and derivatives thereof and peptide antagonists such as CGRP 8-37 and CGRP 28-3; antagonists of pro-nociceptive peptide neurotransmitter receptor NK1, including non-peptide antagonists such as SR140333, CP96346, L-760735; RP 67580, WIN 51708; MK869, and derivatives thereof and peptide antagonists such as N-acetyl tryptophan, D-Pro9-[Spiro-y-lactam]-Leu10,Trp11-Physalaemin(1-11), Tyr-D-Phe-Phe-D-His-Leu-Met-NH$_2$ (Sendide) and spantide II; antagonists of pro-nociceptive peptide neurotransmitter receptor NK2, including non-peptide antagonists such as SR 48968 and derivatives thereof and peptide antagonists such as PhCO-Ala-Ala-D-Trp-Phe-D-Pro-Pro-Nle-NH$_2$ (GR98400), [Tyr5,D-Trp6,8,9,Lys10]-NKA (4-10) (MEN10376) and derivatives thereof; antagonists of pro-nociceptive peptide neurotransmitter receptor Y1-5, including non-peptide antagonist benextramine and peptide antagonists (Ile-Glu-Pro-Dpr-Tyr-Arg-Leu-Arg-Tyr-NH$_2$)$_2$, cyclic (2,4'),(2',4)-diamide (1229U91 or GW1229), PYX-2, D-Tyr (27,36), D-Thr (32)] NPY (27-36) (D-NPY(27-36), 3-(5,6,7,8-tetrahydro-9-isopropyl-carbazol-3-yl)-1-methyl-1-(2-pyridin-4-yl-ethyl)-urea hydrochloride (FMS586 and derivatives thereof); antagonists of pro-nociceptive peptide neurotransmitter receptors VPAC2, VPAC1 and PAC1, including peptide antagonists VIP(6-28), Ac His(1) [D-Phe(2), K(15), R(16), L(27)] VIP (3-7)/GRF (8-27); antagonists of pro-nociceptive peptide neurotransmitter receptors Gal1-3 and GalR1-3, including non-peptide antagonists SNAP 37889, SNAP 398299, galnon and derivatives thereof. Additional active agents may include agonists or antagonists of vasopressin, corticotropin releasing hormone (CRH), growth hormone releasing hormone (GHRH), luteinizing hormone releasing hormone (LHRH), somatostatin growth hormone release inhibiting hormone, thyrotropin releasing hormone (TRH), glial-derived neurotrophic factor (GDNF), brain-derived neurotrophic factor (BDNF), nerve growth factor (NGF), neurotrophin-3 (NT-3), pancreatic polypeptide, peptide tyrosine-tyrosine, glucogen-like peptide-1 (GLP-1), peptide histidine isoleucine (PHI), pituitary adenylate cyclase activating peptide (PACAP), brain natriuretic peptide, cholecystokinin (CCK), islet amyloid polypeptide (IAPP) or amylin, melanin concentrating hormone (MCH), melanocortins (ACTH, α-MSH and others), neuropeptide FF (F8Fa), neurotensin, parathyroid hormone related protein, Agouti gene-related protein (AGRP), cocaine and amphetamine regulated transcript (CART)/peptide, 5-HT-moduline, hypocretins/orexins, nociceptin/orphanin FQ, ocistatin, prolactin releasing peptide, secretoneurin, urocortin and derivatives and analogues thereof.

Accordingly, described herein are methods for the treatment of headache pain or trigeminal neuralgia in an individual comprising administering to the individual an effective amount of an oxytocin peptide. In general, the methods administer an oxytocin peptide for prevention or treatment of head pain. In some aspects the head pain is a result of primary and secondary headaches. In some examples the primary headache is a vascular headache or a tension-type headache. In some examples the vascular headache is a migraine or a cluster type headache. In other examples, the head pain is a result of trigeminal neuralgia. Some aspects of the invention include methods wherein the administration results predominantly in analgesia to the facial or head region and in alleviation of headache pain. Some aspects of the invention include methods wherein an oxytocin peptide is administered prior to headache pain for preventive treatment. In other aspects of the invention an oxytocin peptide is administered in combination with at least one additional active agent.

Administration

Described herein are methods for the treatment of headache pain or trigeminal neuralgia in an individual comprising administering to the individual an oxytocin peptide to mucosa tissue or epithelium within the oral cavity, the nasal cavity, within or around the eye or to the skin. The oral mucosal tissues include, but are not limited to, the gingiva (gums), the floor of the oral cavity, the cheeks, the lips, the tongue, the teeth or a combination thereof. The methods can include administering an oxytocin peptide to conjunctiva or other mucosal tissues around the eye. The tissues or epithelium include, but are not limited to, the conjunctiva, the lacrimal gland, the nasolacrimal ducts, the mucosa of the upper or lower eyelid, the eye, or a combination thereof. An oxytocin peptide that is administered to the conjunctiva but not absorbed completely through the conjunctival mucosa can drain through the nasolacrimal ducts into the nose wherein it can be absorbed by mucosal tissue within the nasal cavity. An oxytocin peptide can be administered to the mucosa tissue within the nasal cavity. Suitable regions include, but are not limited to, the inferior two-thirds of the nasal cavity.

Intranasal drug delivery has been a topic of research and development for many years, although it has been only within the past decade that carrier systems have been devised which make delivery of substances effective. (Sayani and Chien (1996) *Critical Reviews in Therapeutic Drug Carrier Systems,* 13:85-184). Intranasal delivery has a number of advantageous features including comparatively high bioavailability, rapid kinetics of absorption and avoidance of a first-pass effect in the liver. In regard to patient compliance and ease of use, intranasal administration provides a simple, rapid and non-invasive mode of application. In some aspects, intranasal administration can allow for delivery of an oxytocin peptide to the nasal cavity and in other aspects, intranasal administration can allow for targeted delivery to the trigeminal nerve. Targeted delivery to the trigeminal nerve and preferably not the olfactory region can reduce the amount of drug entering the CNS or systemic circulation thereby reducing or eliminating potential undesirable CNS effects or systemic side effects. Targeted delivery to the trigeminal nerve can also reduce the effective dosage necessary to achieve analgesia in the facial or head regions wherein lower effective dosages will further reduce any potential CNS or systemic side effects.

Some aspects of the present invention include methods for treatment of headache pain or trigeminal neuralgia in an individual comprising administering to the individual an oxytocin peptide by intranasal administration. In some examples the pain is associated with a migraine. In other examples the pain is associated with a cluster headache. In yet other examples the pain is associated with a tension-type headache. In yet other examples the pain is associated with trigeminal neuralgia.

Some aspects of the present invention include methods for prevention of headache pain or trigeminal neuralgia in an individual comprising administering to the individual an oxytocin peptide by intranasal administration. In some examples the individual is experiencing a migraine-associated aura and the individual is administered an oxytocin peptide prior to the onset of a migraine headache. In other examples an individual is experiencing a series of cluster headaches and the individual is administered an oxytocin peptide after the cluster series has started to prevent or decrease the intensity or frequency of successive headaches in the series. In other examples the individual is experiencing bursts of pain from a trigeminal neuralgia attack and the individual is administered an oxytocin peptide to prevent further attacks.

Some aspects of the present invention include methods for treatment of headache pain or trigeminal neuralgia in an individual comprising administering to the individual an oxytocin peptide by intranasal administration wherein the administration results predominantly in analgesia to the facial or head region and in alleviation of headache pain. In some examples, the methods can administer an oxytocin peptide to the nasal cavity of an individual, in particular to the inferior region of the nasal cavity, to promote delivery to the trigeminal nerve with minimal delivery to the olfactory nerve.

Within the oral cavity, the buccal or sublingual delivery routes are convenient choices for drug delivery as they are user-friendly and non-invasive. Some of the advantages include i) less proteolytic activity in the oral cavity as compared to some other routes thereby avoiding the problems of enzymatic degradation of peptide and protein drugs and ii) bypassing the liver first pass effect. Drug delivery to the mucosal tissue around the eye or to the conjunctiva is another convenient choice for drug delivery that is non-invasive.

Some aspects of the present invention include methods for treatment of headache pain or trigeminal neuralgia in an individual comprising administering an effective amount of an oxytocin peptide to the conjunctiva or other mucosal tissues around the eye.

Transdermal drug delivery or administration of a therapeutic agent to the skin has become a proven technology over the last 20 years. Transdermal drug delivery offers controlled release of a drug to the patient and transdermal patches are user-friendly, convenient, painless, and offer multi-day dosing which usually results in improved patient compliance. The methods can include administering an oxytocin peptide to skin of the face, head or body. An oxytocin peptide can be administered to the skin of the face, scalp or temporal region. Suitable skin of the face includes skin of the chin, the upper lip, the lower lip, the forehead, the nose, the cheek, the skin around the eyes, the upper eyelid, the lower eyelid or combinations thereof. Suitable skin of the scalp includes the front of the scalp, the scalp over the temporal region, the lateral part of the scalp, or combinations thereof. Suitable skin of the temporal region includes the temple and the scalp over the temporal region and combinations thereof.

Intradermal administration of a therapeutic agent is defined as within or between the layers of skin. In contrast, subcutaneous administration is defined as beneath the initial layer of skin. Administration of therapeutic agents by intradermal or subcutaneous injection are common means of drug delivery by one skilled in the art.

In some aspects of the invention a vasoconstrictor is used to decrease systemic uptake of an oxytocin peptide. The vasoconstrictor can be included in a pharmaceutical composition to decrease systemic uptake of the oxytocin peptide. Alternatively, the vasoconstrictor may be delivered to the mucosal or dermal surface separately from the pharmaceutical composition. Vasoconstrictors are compounds that constrict blood vessels and capillaries and decrease blood flow. They can be used to increase concentration of an agent at a desired site by inhibiting movement of the agent into the bloodstream and thereby reducing systemic uptake and distribution of the agent. Vasoconstrictors can be used to decrease the effective dosage of an agent needed to achieve analgesia by limiting systemic distribution and concentrating the agent in a localized area, i.e. the facial and head regions. Accordingly, a vasoconstrictor can be administered before administration of an oxytocin peptide or can be co-administered with an oxytocin peptide. Vasoconstrictors may include, but are not limited to, phenylephrine hydrochloride, tetrahydrozoline hydrochloride, naphazoline nitrate, oxymetazoline hydrochloride, tramazoline hydrochloride, ergotamine, dihydroergotamine, endothelin-1, endothelin-2, epinephrine, norepinephrine and angiotensin.

Some aspects of the present invention include methods wherein a vasoconstrictor is administered to the nasal cavity of an individual prior to administration of an oxytocin peptide, wherein administration of the vasoconstrictor decreases systemic distribution of the oxytocin peptide. In some examples, the methods can co-administer a vasoconstrictor and an oxytocin peptide to the nasal cavity of an individual, wherein administration of the vasoconstrictor decreases systemic distribution of the oxytocin peptide. In other examples, the methods can administer a vasoconstrictor to the nasal cavity of an individual prior to or co-administer with an oxytocin peptide, wherein administration of the vasoconstrictor decreases systemic uptake and distribution of the oxytocin peptide thereby decreasing the effective dosage requirement of the oxytocin peptide necessary to achieve analgesia in the facial or head region and to alleviate headache pain or trigeminal neuralgia pain.

In some aspects of the present invention administration of an oxytocin peptide targeted for a predominantly regional analgesic effect can result in prevention or alleviation of headache pain or trigeminal neuralgia without numbness as compared to local anesthetics or the strong sedative effect associated with narcotic type drugs. Since the trigeminal nerve transmits most of the sensory signals of the face and head, administration of an oxytocin peptide targeted to the trigeminal nerve can localize the analgesic effect to the face and head region. Targeted delivery can also decrease the amount of oxytocin peptide administered to an individual to achieve an analgesic effect, and can decrease any potential undesirable CNS effects or systemic side effects. More effective or efficient delivery of an oxytocin peptide to the trigeminal nerve can decrease the total dose of the peptide administered to a subject suffering from headache pain or trigeminal neuralgia. Effective targeted delivery of an oxytocin peptide to the trigeminal nerve can decrease the systemic distribution of the agent wherein any potential undesirable CNS effects or systemic side effects are minimized or eliminated.

Accordingly, provided herein are methods for treatment of headache pain or trigeminal neuralgia in an individual comprising administering to the individual an oxytocin peptide wherein the administration is targeted to the trigeminal nerve system and results predominantly in analgesia to the facial or head region as compared to analgesic effects in other parts of the body and in alleviation of head pain.

Pharmaceutical Composition

While it is possible to administer an oxytocin peptide alone, there are situations wherein it is advantageous to present it as part of a pharmaceutical composition. Thus, in some aspects of the present invention, an oxytocin peptide is administered as a pharmaceutical composition. The pharmaceutical composition can comprise an oxytocin peptide at a therapeutically effective dose together with one or more pharmaceutically acceptable carriers and optionally other ingredients. A suitable carrier is one which does not cause an intolerable side effect, but which allows oxytocin to retain its pharmacological activity in the body. A carrier may also reduce any undesirable side effects of oxytocin. A suitable carrier should be stable, i.e., incapable of reacting with other ingredients in the formulation. A suitable carrier should have minimal odor or fragrance or fragrance or a positive (pleasant) odor. A suitable carrier should not irritate the mucosa, epithelium, underlying nerves or provide a health risk. It may be an accepted transcutaneous or percutaneous carrier or vehicle, because any carrier that can effectively penetrate the stratum corneum of the skin should be highly efficacious in not only penetrating mucosa, but also allowing rapid absorption of substances into the submucosal tissues, nerve sheaths and nerves.

Suitable nontoxic pharmaceutically acceptable carriers will be apparent to those skilled in the art of pharmaceutical formulations. Also see *Remington: The Science and Practice of Pharmacy,* 20th Edition, Lippincott, Williams & Wilkins (2000). Typical pharmaceutically acceptable carriers include, but are not limited to, mannitol, urea, dextrans, lactose, potato and maize starches, magnesium stearate, talc, vegetable oils, polyalkylene glycols, ethyl cellulose, poly(vinylpyrrolidone), calcium carbonate, chitosan, ethyl oleate, isopropyl myristate, benzyl benzoate, sodium carbonate, gelatin, potassium carbonate, silicic acid, and other conventionally employed acceptable carriers. Other carriers include, but are not limited to, phosphatidylcholine, phosphatidylserine, and sphingomyelins.

The choice of a suitable carrier will depend on the exact nature of the particular formulation desired, e.g., whether the drug is to be formulated into a liquid solution (e.g., for use as drops, for use in an injection, as a spray or impregnated in a nasal tampon, or other agent-impregnated solid), a suspension, a ointment, a film or a gel. If desired, sustained-release compositions, e.g. sustained-release gels, films, transdermal patches, etc. can be readily prepared. The particular formulation will also depend on the route of administration. The agent can be administered to the nasal cavity as a powder, a granule, a solution, a cream, a spray, a gel, a film, an ointment, an infusion, a drop or a sustained-release composition. For buccal administration, the composition can take the form of tablets or lozenges formulated in a convention manner. For sublingual administration, the composition can take the form of a bioadhesive, a spray, a powder, paint or a swab applied to or under the tongue. For administration to the conjunctiva or other mucosal tissues around the eye, the composition can be applied as an ointment, a solution or a drop. For administration to the skin, the composition can be applied as a topical ointment, a topical gel, a lotion, a cream, a solution, a spray, a paint, a film, a foil, a cosmetic, a patch or a bioadhesive.

Liquid carriers include, but are not limited to, water, saline, aqueous dextrose, and glycols particularly (when isotonic) for solutions. The carrier can also be selected from various oils, including those of petroleum, animal, vegetable or synthetic origin, (e.g. peanut oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, antioxidants, chelating agents, wetting agents, emulsifying agents, dispersing agents, jelling agents, salts for adjusting osmotic pressure, buffers, and the like. Where the carrier is a liquid, it is preferred that the carrier be hypotonic or isotonic with body fluids and have a pH within the range of 4.5-8.5. Where the carrier is in powdered form, it is preferred that the carrier be within an acceptable non-toxic pH range. The use of additives in the preparation of peptide and/or protein-based compositions, particularly pharmaceutical compositions, is well-known in the art.

The lists of carriers and additives discussed herein are by no means complete and a worker skilled in the art can choose carriers and excipients from the GRAS (generally regarded as safe) list of chemicals allowed in pharmaceutical preparations and those that are currently allowed in topical and parenteral formulations. (See also Wang et al., (1980) *J. Parent. Drug Assn.,* 34:452-462; Wang et al., (1988) *J. Parent. Sci. and Tech.,* 42:S4-S26).

Other forms of compositions for administration include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration, for example a spray, paint, or swab applied to the mucosa or epithelium. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the oral or nasal cavity. Such adhesives can include, but are not limited to, hydroxypropyl cellulose, hydroxypropyl methylcellulose, hydroxy ethylcellulose, ethylcellulose, carboxymethyl cellulose, dextran, gaur gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition can be formulated in a sustained-release form to prolong the presence of the active agent in the treated individual. Many methods of preparation of a sustained-release formulation are known in the art and are disclosed in Remington's Pharmaceutical Sciences (see above). Generally, the agent can be entrapped in semi-permeable matrices of solid hydrophobic polymers. The matrices can be shaped into films or microcapsules. Matrices can include, but are not limited to, polyesters, co-polymers of L-glutamic acid and gamma ethyl-L-glutamate, polylactides, polylactate polyglycolate, hydrogels, non-degradable ethylene-vinyl acetate, degradable lactic acid-glycolic acid copolymers, hyaluronic acid gels, and alginic acid suspensions. Suitable microcapsules can also include hydroxymethylcellulose or gelatin and poly-methyl methacrylate. Microemulsions or colloidal drug delivery systems such as liposomes and albumin microspheres can also be used. Some sustained-release compositions can use a bioadhesive to retain the agent at the site of administration.

To further enhance the mucosal delivery of a pharmaceutical composition comprising an oxytocin peptide, an enzyme inhibitor, particularly proteases inhibitors, can be included in the formulation. Protease inhibitors may include, but are limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH2, DAPT, diprotin A and B, ebelactone A and B, foroxymithine, leupeptin, pepstatin A, phosphoramidon, aprotinin, puromycin, BBI, soybean trypsin inhibitor, phenylmethylsulfonyl fluoride, E-64, chymostatin, 1,10-phenanthroline, EDTA and EGTA.

To enhance delivery into or across a mucosal surface and/or absorption of a pharmaceutical composition comprising an oxytocin peptide, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of an oxytocin peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

These additional agents and compounds can be coordinately administered or combinatorially formulated with an oxytocin peptide. Accordingly, some aspects of the present invention include methods wherein an oxytocin peptide is administered as a pharmaceutical composition that comprises protease inhibitors, absorption enhancers, vasoconstrictors or combinations thereof. The pharmaceutical composition can be administered to the nasal cavity, oral cavity, to conjunctiva or other mucosal tissues around the eye or to the skin. The pharmaceutical composition can be administered by an intranasal route. The pharmaceutical composition can be administered by a buccal or sublingual route. The pharmaceutical composition can be administered by a transdermal route. The pharmaceutical composition can be administered by more than one route. The pharmaceutical composition can include at least one protease inhibitor, at least one absorption enhancer, at least one vasoconstrictor or combinations thereof. The pharmaceutical composition can be co-administered with a vasoconstrictor or administered after the vasoconstrictor has been delivered.

Delivery Systems

An oxytocin peptide or a pharmaceutical composition comprising an oxytocin peptide may be dispensed to the buccal or sublingual surfaces in a number of different formulations or dosage forms including, but not limited to, fast-melting tablets, liquid-filled capsules, liquid sprays or lozenges. Alternatively, a pharmaceutical composition can be delivered to the mucosa of the oral cavity by direct placement of the composition in the mouth, for example, with a gel, a film, an ointment, a dropper, or a bioadhesive strip or patch.

In some aspects of the present invention, the methods comprise administering to an individual a pharmaceutical composition wherein administration to the buccal and/or sublingual mucosal surfaces of the oral cavity is by a delivery device. The delivery device can include, but is not limited to, unit dose containers, pump sprays, droppers, squeeze bottles, airless and preservative-free sprays, nebulizers, dose inhalers and pressurized dose inhalers. The delivery device can be metered to administer an accurate effective dosage amount (as described below) to the oral cavity. In some aspects, an accurate effective dosage amount is contained within a capsule, tablet, lozenge, or bioadhesive patch that is placed directly within the oral cavity.

An oxytocin peptide or a pharmaceutical composition comprising an oxytocin peptide may be dispensed to the conjunctiva or to other mucosal tissues around the eye in a number of different formulations such as a liquid drop, a gel, a film, an ointment or a bioadhesive patch or strip. Thus, in some aspects of the present invention the methods comprise administering to an individual a pharmaceutical composition wherein administration is directed to the conjunctiva or other mucosal tissues around the eye. In some aspects, an accurate effective dosage amount is contained within a drop, a gel, a film, an ointment or a bioadhesive patch that is placed directly onto the mucosal tissues around the eye.

An oxytocin peptide or pharmaceutical composition comprising an oxytocin peptide may be administered to the skin or scalp in a number of different formulations such as a liquid, a spray, a gel, a film, an ointment or a bioadhesive patch or strip. Thus, in some aspects of the present invention the methods comprise administering to an individual a pharmaceutical composition wherein administration is directed to the skin of the face, scalp or body. In some aspects, an accurate effective dosage amount is contained within a drop, a gel, a film, an ointment or a bioadhesive transdermal patch that is placed directly onto the skin. In some aspects, a pharmaceutical composition may be administered to the skin intradermally by injection. In other aspects the composition may be administered to the skin subcutaneously by injection.

An oxytocin peptide or a pharmaceutical composition comprising an oxytocin peptide may be dispensed intranasally as a powdered or liquid nasal spray, suspension, nose drops, a gel, film or ointment, through a tube or catheter, by syringe, by packtail, by pledget (a small flat absorbent pad), by nasal tampon or by submucosal infusion. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. It is important that the delivery device protect the drug from contamination and chemical degradation. The device should also avoid leaching or absorption as well as provide an appropriate environment for storage. Each drug needs to be evaluated to determine which nasal drug delivery system is most appropriate. Nasal drug delivery systems are known in the art and several are commercially available.

An oxytocin peptide or a pharmaceutical composition comprising an oxytocin peptide may be conveniently delivered in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the pharmaceutical composition. In the case of a pressurized aerosol, the dosage unit may be controlled by providing a valve to deliver an accurately metered amount.

The means to deliver an oxytocin peptide or pharmaceutical composition comprising an oxytocin peptide to the nasal cavity as a powder can be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the nasal cavity.

Nasal delivery devices can be constructed or modified to dispense an oxytocin peptide or a pharmaceutical composition comprising an oxytocin peptide wherein the oxytocin peptide or the composition is delivered predominantly to the inferior two-thirds of the nasal cavity. For example, the angle of dispersion from a delivery device such as a nebulizer or an insufflator can be set so that the pharmaceutical composition is mechanically directed to the inferior two-thirds of the nasal cavity, and preferably away from the superior region of the nasal cavity. Alternatively, an oxytocin peptide or a pharmaceutical composition comprising an oxytocin peptide can be delivered to the inferior two-thirds of the nasal cavity by direct placement of the composition in the nasal cavity, for example, with a gel, an ointment, a nasal tampon, a dropper, or a bioadhesive strip.

Thus in some aspects of the present invention, the methods comprise administering to an individual an oxytocin peptide or pharmaceutical composition comprising an oxytocin peptide wherein administration to the nasal cavity is by a nasal delivery device. The nasal delivery device can include, but is not limited to, unit dose containers, pump sprays, droppers, squeeze bottles, airless and preservative-free sprays, nebulizers, dose inhalers, pressurized dose inhalers, insufflators, and bi-directional devices. The nasal delivery device can be metered to administer an accurate effective dosage amount (as described below) to the nasal cavity. The nasal delivery device can be for single unit delivery or multiple unit delivery. In some aspects of the present invention, the nasal delivery device can be constructed whereby the angle of dispersion of a pharmaceutical composition is mechanically directed towards the inferior two-thirds of the nasal cavity thereby minimizing delivery to the olfactory region. In some aspects of the present invention, the nasal delivery device may be activated only on exhalation, thus limiting the inhalation induced and potentially undesirable distribution of the pharmaceutical composition. In some aspects of the present invention, the pharmaceutical composition is a gel, film, cream, ointment, impregnated in a nasal tampon or bioadhesive strip whereby the composition is placed in the inferior two-thirds of the nasal cavity. In some aspects of the present invention, the methods include intranasal administration of an oxytocin peptide or a pharmaceutical composition comprising an oxytocin peptide wherein the administration uses a nasal delivery device with an angle of dispersion that mechanically directs the agent to the inferior two-thirds of the nasal cavity wherein the oxytocin peptide is administered after a vasoconstrictor. In some aspects of the present invention, the methods include intranasal administration of an oxytocin peptide or pharmaceutical composition comprising an oxytocin peptide wherein the administration uses a nasal delivery device with an angle of dispersion that mechanically directs the agent to the inferior two-thirds of the nasal cavity wherein the oxytocin peptide is co-administered with a vasoconstrictor.

Dosages

An oxytocin peptide is administered in a dose sufficient to provide a therapeutically effective amount to an individual suffering from headache pain or trigeminal neuralgia. In some aspects, an oxytocin peptide can be administered in a dose that results in analgesia to the facial or head regions with minimal global CNS effects or systemic side effects. A therapeutically effective dose of an oxytocin peptide can be determined empirically and depends on the type and severity of the headache pain, the route of administration, and the size, weight, age and overall health of the patient, as is within the skill of one in the art such as a medical practitioner.

The amount of an oxytocin peptide administered as a unit dose will depend upon the type of pharmaceutical composition being administered, for example, a solution, a suspension, a gel, a film, an emulsion, a powder, or a sustained-release formulation. In some examples, the effective dosage will be lower than dose amounts needed for oral, intravenous, intramuscular or subcutaneous administration, since transmucosal or transdermal delivery may allow for a more concentrated level of the oxytocin peptide within the facial and head region. The quantity of formulation needed to deliver the desired dose will also depend on the concentration of the oxytocin peptide in the composition. Such determinations are within the skill of one in the art.

The therapeutic dosage of an oxytocin peptide in the pharmaceutical compositions used in the methods of the present invention will depend on a number of factors such as the chemical composition and/or modification of the oxytocin peptide, its bioavailability by the chosen route of administration, its efficacy, the desired frequency of administration combined with the desired single dosage of the formulation and whether the oxytocin peptide is administered in combination with other active agent(s). Particularly, the dosage of an oxytocin peptide will be chosen to maximize alleviation of headache pain or trigeminal neuralgia. Pharmacological data can be obtained from animal models and clinical trials with normal human volunteers or patients experiencing headache pain or trigeminal neuralgia by one with skill in the art.

Experimental models to test for analgesic activity of agents are known in the art. Animal models comprise tests which include, but are not limited to, acetic acid writhing, phenylquinone writhing, tail-flick, paw withdrawal and ear/face withdrawal wherein the pain receptor activation is induced by such compounds as acetic acid, phenylquinone, formalin or capsaicin, or by thermal activators such as a hot plate or a laser. In particular, models for facial or head pain utilizing tests such as orofacial delivery of capsaicin, orofacial delivery of formalin, or delivery of thermal heat to the ear or the face are available. Models can be used to determine optimal dosage ranges wherein an analgesic agent results in analgesia in the facial or head region with minimal analgesia at a systemic site, i.e. the paw. Further, models can be used to administer an analgesic agent by a particular delivery route, e.g. intranasally, and test for analgesic effect at the ears or the face and at the hindpaws. Thus, one model can be used to test for analgesic activity of an analgesic agent after administration of a pharmaceutical composition wherein withdrawal latencies at the ear or face will determine localized analgesia while withdrawal latencies at the hindpaw will determine systemic distribution and analgesia.

As stated above, an effective amount of an oxytocin peptide will depend on the form and composition being used in the method. Preferably the effective amount of an oxytocin peptide administered transmucosally or transdermally is lower than dosages used when the agent is delivered by other routes (e.g. oral, intravenous, intramuscular or subcutaneous). For example, dosages used for administration of an oxytocin peptide can include, but are not limited to, an effective amount within the dosage range of about 0.1 IU to about 150 IU, or within 1 IU to about 100 IU, or within 10 IU to about 80 IU, or within about 25 IU to about 50 IU, or within about 1 IU to about 40 IU, or within about 1 IU to about 30 IU, or within about 4 IU to about 16 IU, or within about 4 IU to about 24 IU.

Dosages can be administered in a single dose or in multiple doses, for example, dosages can be administered two, three, four, up to ten times daily depending on the type and severity of headache pain being treated as well as on individual susceptibility. Dosages can be administered in a sustained release formulation which may allow for an oxytocin peptide to be administered less frequently such as six times a week, five times a week, four times a week, three times a week, twice a week, or once a week.

Thus some aspects of the present invention include methods for treatment of headache pain or trigeminal neuralgia comprising administering to an individual an effective amount of an oxytocin peptide. The oxytocin peptide can be administered within a dosage range of about 0.1 IU to about 150 IU, or within 0.1 IU to about 100 IU, or within 1 IU to about 100 IU, or within 10 IU to about 80 IU, or within about 25 IU to about 50 IU, or within about 1 IU to about 40 IU, or within about 1 IU to about 30 IU, or within about 4 IU to about 16 IU, or within about 4 IU to about 24 IU. In some examples the oxytocin peptide is administered in a dose of about 4 IU. In some examples, the dose is about 8 IU. In other examples the dose is about 16 IU. In some examples, the dose is about 24 IU.

In some aspects of the present invention, a composition comprising an oxytocin peptide may further comprise an additional active agent, wherein the oxytocin peptide and the additional active agent(s) are administered as a mixture, separately and simultaneously, or separately in any order. In some examples the composition comprising an oxytocin peptide is administered in combination with at least one additional active agent. In other examples, the composition comprising an oxytocin peptide is administered in combination with at least two additional active agents. In other example, the composition comprises an oxytocin peptide administered in combination with diclofenac.

To determine the therapeutic effect of an oxytocin peptide or a composition comprising an oxytocin peptide, the "visual analogue scale" (VAS) may be used to assess the reduction or alleviation of pain after administration of the oxytocin. VAS is a 10 cm horizontal or vertical line with word anchors at each end, such as "no pain" and "pain as bad as it could be". A subject or patient is asked to make a mark on the line to represent pain intensity. This mark is converted to distance in either centimeters or millimeters from the "no pain" anchor to give a pain score that can range from 0-10 cm or 0-100 mm. The VAS may also be set up as an 11 point numerical pain rating scale wherein 0 equals "no pain" and 10 equals the "worst pain imaginable". Using the VAS, an analgesic agent, e.g. oxytocin, is considered to have an analgesic effect when there is a change of about 30% or more, for example a change from 9 to 7 or from 5 to 3.5.

Therapeutic Uses

Head pain can arise from a variety of medical conditions including but not limited to, primary headaches such as migraine, cluster headache, tension or stress headache, secondary headaches caused by specific conditions such as neoplastic and infectious diseases, toxin ingestion or over-consumption of alcohol and trigeminal neuralgia. As discussed herein, the most common type of primary vascular headache is migraine with cluster headache being less common but equally debilitating. Tension or "stress"-type headaches are believed to be the most common headache type overall in regard to affecting the largest number of individuals. The characteristics of these headaches or headache disorders are summarized in Table 1.

TABLE 1

|  | Migraine | Tension | Cluster | Trigeminal Neuralgia |
| --- | --- | --- | --- | --- |
| Patho-physiology | Trigemino-vascular pathway | Myo-facial pathway | Trigemino-autonomic pathway | Trigeminal nerve pathway |

TABLE 1-continued

|  | Migraine | Tension | Cluster | Trigeminal Neuralgia |
| --- | --- | --- | --- | --- |
| Laterality | Unilateral (60%) | Bilateral | Unilateral (100%) | Unilateral |
| Intensity | Moderate to severe | Mild to Moderate | Severe | Severe |
| Pain Characteristic | Pulsating (50%) | Pressing | Boring, piercing | Stabbing Electric shock-like |
| Duration | 4-72 hours | Minutes to days | 15-180 minutes Several per a day | 1-2 seconds to 2 minutes Many per a day |
| Physical Activity Effect | Aggravated by activity | No effect | Patients are restless | Minor movements can bring on attack |
| Associated Symptoms | Nausea Photophobia Phonophobia |  | Conjuctival injection Lacrimation Nasal congestion Rhinorrhea Facial sweating Miosis Ptosis Eyelid edema |  |

Headache pain and trigeminal neuralgia are often not effectively treated with current medications and new methods for pain relief are needed. Accordingly, some aspects of the present invention include methods for treatment of headache pain or trigeminal neuralgia by administration of an effective amount of an oxytocin peptide wherein the administration results in analgesia to the facial or head region. The oxytocin peptide can be administered to a patient with a headache disorder including, but not limited to, migraine, cluster headache, tension headache, secondary types of headache and trigeminal neuralgia.

Accordingly, in some aspects of the present invention, the methods comprise administering an oxytocin peptide or a pharmaceutical composition comprising an oxytocin peptide to an individual for treatment of pain associated with migraine. In some aspects of the present invention, the methods comprise administering an oxytocin peptide or a pharmaceutical composition comprising an oxytocin peptide to an individual for treatment of pain associated with a cluster headache. In some aspects of the present invention, the methods comprise administering an oxytocin peptide or a pharmaceutical composition comprising an oxytocin peptide to an individual for treatment of pain associated with a tension headache. In some aspects of the present invention, the methods comprise administering an oxytocin peptide or a pharmaceutical composition comprising an oxytocin peptide to an individual for treatment of pain associated with a secondary type of headache. In some aspects of the present invention, the methods comprise administering an oxytocin peptide or a pharmaceutical composition comprising an oxytocin peptide to an individual for treatment of pain associated with trigeminal neuralgia. In some aspects of the present invention, the methods comprise prophylactic treatment for migraine-associated pain comprising administering an oxytocin peptide or a pharmaceutical composition comprising an oxytocin peptide to an individual experiencing a migraine-associated aura prior to onset of a migraine headache. In some aspects of the present invention, the methods comprise prophylactic treatment for cluster headache pain comprising administering an oxytocin peptide or a pharmaceutical composition comprising an oxytocin peptide to an individual after a cluster series has started but prior to successive headaches in the cluster series. In some aspects of the present invention, the methods comprise prophylactic treatment for trigeminal neuralgia pain comprising administering an oxytocin peptide or a pharmaceutical composition comprising an oxytocin peptide to an individual after trigeminal neuralgia attack but prior to successive attacks.

Kits

Provided herein are kits for carrying out any of the methods described herein. Kits are provided for use in treatment and/or prevention of headache and headache or head pain disorders. Kits of the invention comprise an oxytocin peptide in suitable packaging. Other kits of the invention may further comprise at least one additional analgesic agent. Kits may further comprise a vasoconstrictor, at least one protease inhibitor and/or at least one absorption enhancer. Some kits may further comprise a delivery device, including but not limited to, a device for intranasal administration. Other kits may further comprise instructions providing information to the user and/or health care provider for carrying out any one of the methods described herein.

Kits comprising a single component, for example an oxytocin peptide, will generally have the component enclosed in a container (e.g., a vial, ampoule, or other suitable storage container). Likewise, kits including more than one component may also have the reagents in containers (separately or in a mixture).

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

Example 1

Activity of an analgesic agent can be tested in a rat model by studying treatment-induced changes in latencies (times) of withdrawal in response to noxious heating of the skin, typically applying a stimulus to an ear or a hindpaw. Thus, application of coherent or non-coherent (non-laser) radiant heat to the ear or hindpaw will elicit rapid withdrawal movements. Latencies of withdrawal have been demonstrated to be sensitive to analgesic treatments, such that analgesics increase the latency to withdrawal. Transmucosal or transdermal administration of analgesic agents can be tested for regional and/or systemic analgesia. After administration of an analgesic agent an increase in latency to withdrawal time of the ear would indicate regional analgesia. A change in the latency to withdrawal time of the hindpaw would indicate whether there was a systemic analgesic effect, i.e. no change in the latency to withdrawal time indicates no systemic effect, while an increase in latency to withdrawal time would indicate a systemic effect.

Rats are housed in a 12/12-hour light/dark environment and are provided food and water ad libitum. Efforts are made to minimize discomfort and reduce the number of animals used. Rats are lightly anesthetized with urethane and placed with minimal restraint on a heating pad to maintain their body temperature at 37° C. A laser beam is directed via a fiber optic cable to the rostral external part of both ears. Characteristic responses to laser irradiation are a retraction or withdrawal of the stimulated ear for 1-3 seconds after a thermal stimulus by the laser. Laser stimulation is terminated rapidly after response of the stimulated ear or after a maximal response (cut-off) latency of 30 seconds to prevent tissue damage.

For baseline testing of latency withdrawal responses to the ear, 3 pulses are applied to each ear. The stimulation site is changed after each pulse allowing at least 2 minutes in between 2 stimuli on the same ear. For baseline testing of latency withdrawal responses to the hindpaw, 3 pulses are applied to the hindpaw. The stimulation site is changed after each pulse allowing at least 2 minutes in between 2 stimuli on the same hindpaw. Testing sessions are videotaped for off-line analysis of responses. The off-line analysis is performed by an investigator who determines the latency of withdrawal responses to the laser stimulation and who is blinded to the treatment groups.

After measuring baseline latencies, analgesic agents are administered intranasally. This involves 5 equal 10 µl applications to the nose by pipette for a total volume of 50 µl over 20 minutes. The effect of different doses of an agent (e.g. 10 µg oxytocin) on latency responses is examined. To assess the local analgesic effect, the latency of withdrawal response to noxious heating of the ear is tested at various time points after agent administration. To assess the systemic analgesic effect, the latency of withdrawal response of hindpaws to noxious heating is tested at various time points after agent administration.

Example 2

Sprague-Dawley rats (Charles River Laboratories) were lightly anesthetized with urethane and placed with minimal restraint on a heating pad to maintain their body temperature at 37° C. A laser beam was directed via a fiber optic cable to the rostral external part of both ears or to the hindpaws as described above. Baseline withdrawal latencies were measured by delivering 4 separate stimuli with a resting period of approximately 15 minutes between each stimulus. 50 µl of oxytocin in phosphate-buffered saline was intranasally administered in 5 equal 10 µl applications at a dosage of 10 µg. Withdrawal latencies for both ears and hindpaws were tested five minutes after the final application of oxytocin. As described above, testing sessions were videotaped and analyzed. Results demonstrated that intranasal administration of oxytocin at this dosage achieved a regional analgesic effect in the head region without a systemic analgesic effect at the hindpaw.

Rats were intranasally administered 10 µg oxytocin and withdrawal latencies were tested. Each data point represents the average, across 8 animals, of latencies in response to stimulation at a particular time after the beginning of the test. The circles represent the withdrawal latencies after thermal stimulation to the ear in control rats treated with saline. The squares represent the withdrawal latencies after thermal stimulation to the ear in rats treated with 10 µg oxytocin. The triangles represent the withdrawal latencies after thermal stimulation to the hindpaw in the treated rats. (FIG. 1).

Example 3

Upon presentation at the clinic, a patient is asked for a pain assessment (0-10 rating on VAS). The VAS is an 11-point numerical pain rating scale wherein 0 equals "no pain" and 10 equals the "worst pain imaginable". The analgesic agent is self-administered by nasal applicator. Initially, one puff is given in each nostril. After waiting 15 minutes the patient is asked again for a pain rating and any side effects (e.g. sedation) are assessed. If pain is still present, another puff per nostril is self-administered. After another 15 minutes, pain and side-effects are assessed. If pain is still present, two more puffs of agent are self-administered. After 15 minutes, pain is rated again, and side effects are assessed. If pain is still present, a final two puffs are given. After another 15 minutes and at 15, 30 and 60 minutes after that, pain and side-effects are re-assessed.

Example 4

A female patient with severe headaches secondary to adult hydrocephalus and multiple shunt surgeries was seen at the clinic. The patient's pain had been unrelieved by treatment with triptans, ergotamines, and high-dose opiates. The patient presented with a pain rating of 8 out of 10 as assessed by the procedure described herein. The patient self-administered oxytocin intranasally at a dose of 4 IU in 0.2 ml. Within 5 minutes of administering oxytocin, the patient demonstrated mild sedation, which cleared within 10 minutes. The patient's headache pain was significantly reduced by 15 minutes after administration, and was completely gone by 30 minutes. Pain relief lasted approximately 24 hours, only briefly interrupted by mild head pain that occurred with activity. The day after treatment with oxytocin the patient reported some breast tenderness which resolved within 24 hours.

This patient returned to the clinic approximately 1 month later. At this appointment the patient rated the pain as an 8 out of 10. Unbeknownst to her, the patient was first given an intranasal administration of normal saline, in approximately the same volume as used for the oxytocin administration (0.2 ml). No analgesic or other effect was reported by the patient. After waiting 30 minutes, the patient was administered 4 IU of oxytocin intranasally as described above. Within 20-25 minutes, the patient reported that the pain was completely gone. In contrast to the first administration there was no observed sedation, nor was there any breast tenderness the following day. Pain returned approximately 24 hours after treatment.

Example 5

A patient was seen reporting a "stress" or tension headache for which she rated her head pain as a 5 out of 10 as assessed by the procedure described herein. The patient was treated with oxytocin administered intranasally at a dose of 4 IU in 0.2 ml. Approximately 10-15 minutes after administration, the patient reported that the pain was completely gone. The patient reported feeling slightly "giddy" for the first 10 minutes, after which this sensation resolved. The patient reported being pain free for approximately 48 hours.

Example 6

A patient was seen reporting a "hangover" headache which was rated as an 8 out of 10 as assessed by the procedure described herein. The patient was treated with oxytocin administered intranasally at a dose of 24 IU. The patient reported that the headache completely resolved within 15 minutes.

Example 7

A patient was seen reporting having an ongoing strong headache with occasional boring pain on the left side. The pain had lasted for more than 2 weeks and had been diagnosed as a "cluster" headache. The patient was treated with oxytocin administered intranasally at a dose of 16 IU. The patient reported that their headache completely resolved within 15 minutes and relief lasted for 24 hours.

Example 8

A patient was seen after reporting a daily migraine which she rated as a mild to moderate headache with a pain rating of 4 out of 10 as assessed by the procedure described herein. The patient was treated with oxytocin administered intranasally at a dose of 24 IU. The patient reported that the oxytocin decreased the pain to a rating of 2 out of 10.

Example 9

Regional analgesia in the face region after administration of an analgesic agent by intranasal delivery is tested in normal subjects. Study participants are selected based on inclusion/exclusion criteria, history and physical exam, laboratory tests, and other customary procedures. Thermal pain responses are elicited on the face, in particular the cheek, and on an extremity, such as the hand or leg, of healthy normal volunteers, such that temperature thresholds for evoking pain and/or the temperature of maximal pain tolerance can be assessed and baselines established. Increasing doses of an analgesic agent are administered to the subjects and a dose-response curve is calculated for each stimulation site. Changes in thermal pain threshold and tolerance at the two sites can be compared so that the efficacy of an analgesic agent at a given dose in affecting facial and whole-body pain can be determined.

Example 10

Study of intranasal administration of oxytocin for the treatment of trigeminal neuralgia. Ten patients suffering from trigeminal neuralgia are enrolled in a double-blinded, randomized, cross-over study. The total study duration is three weeks, sub-divided into two 1-week trial periods set apart by a 3-day washout period. Five participants are randomized to receive oxytocin nasal spray during the first week and to receive placebo nasal spray during the second week. Five subjects are randomized to the reverse order of drug treatment.

Eligibility for the study is determined by telephone interview and during a first visit at the study center. During the first visit of potential participants at the study center a medical history is taken and a medical exam is performed. In particular, the diagnosis of trigeminal neuralgia is established by one skilled in the art. If participants meet inclusion criteria and no exclusion criteria apply written informed consent is obtained. Demographic and medical data are recorded. Participants are randomized to treatment sequence and receive either oxytocin or saline placebo nasal spray. Participants receive a diary for recording outcome data. Careful instructions are given in regard to the correct application of the nasal spray and the recording of outcome data.

Patients are instructed to apply two puffs of nasal spray in the morning of study day 1 (200 µl or 2 IU or 3.4 µg oxytocin/puff or saline placebo; American Pharmaceutical Partners, Inc, IL). If symptoms persist, patients are instructed to increase the number of puffs by two per treatment day (i.e., 4 puffs on study day 2, 6 puffs on study 3, up to 14 puffs on day 7).

Efficacy measures are assessed daily. Subjects are asked to record the daily intensity and frequency of trigeminal neuralgia attacks (attack=paroxysm of pain, not individual stabs of pain). Subjects are also asked to record the occurrence of adverse events. At the end of a study week, subjects are asked for a global evaluation comparing how they felt during the study week with the pre-trial condition. Patients are also asked whether activities that trigger trigeminal neuralgia attacks have changed when comparing the study week with the pre-trial condition (much increased, increased, same, decreased, much decreased).

At the end of each one week trail period or at any time of a participant's or investigator's request, a follow-up visit at the study center is scheduled. During a follow-up visit all entries on the diary are reviewed and particular questions or concerns relating to the study are discussed.

Example 11

Study of intranasal administration of oxytocin and diclofenac for the treatment of trigeminal neuralgia. The study is conducted as described above in Example 10, ten patients suffering from trigeminal neuralgia are enrolled in a double-blinded, randomized, cross-over study. Five participants are randomized to receive diclofenac and oxytocin nasal spray during the first week and to receive diclofenac and placebo nasal spray during the second week. Five subjects are randomized to the reverse order of drug treatment.

Patients are instructed to apply two puffs of diclofenac followed five minutes later by two puffs of oxytocin nasal spray in the morning of study day 1. Each puff contains 0.2 mg diclofenac (Novartis Ophthalmics, GA) or 2 IU or 3.4 µg oxytocin (American Pharmaceutical Partners, Inc, IL). If symptoms persist, patients are instructed to increase the number of puffs by two per treatment day (i.e., 4 puffs on study day 2, 6 puffs on study 3, up to 14 puffs on day 7).

Efficacy measures are assessed daily as described above for Example 10.

Example 12

Study of intranasal administration of oxytocin for the treatment of migraine. Forty patients suffering from migraine with or without aura are enrolled in a double-blinded, randomized, cross-over study. The total study duration is determined by the time that elapses until a patient has experienced two migraine attacks. Twenty participants are randomized to receive oxytocin nasal spray for treating the first migraine attack and to receive placebo nasal spray for treating the second migraine attack. Twenty subjects are randomized to the reverse order of drug treatment.

Eligibility for the study is determined by telephone interview and during a first visit at the study center. During the first visit of potential participants at the study center a medical history is taken and a medical exam is performed. In particular, the diagnosis of migraine headache with or without aura is established by one skilled in the art. If participants meet inclusion criteria and no exclusion criteria apply written informed consent is obtained. Demographic and medical data are recorded. Participants are randomized to treatment sequence and receive two nasal sprays containing either oxytocin or saline placebo nasal spray. Participants receive a diary for recording outcome data. Careful instructions are given in regard to the correct application of the nasal spray and the recording of outcome data.

Once a patient identifies the onset of a migraine attack, the patient is instructed to administer two puffs of oxytocin or saline nasal spray to each nostril within 5 minutes. Each puff contains 2 IU or 3.4 µg oxytocin (American Pharmaceutical Partners, Inc, Ill.). At the time of drug administration a moderate headache not declining in intensity should be present. Experiencing a mild headache or an aura only should not result in self-administration of the drug. Nasal spray is administered no later than 2 hours after the onset of the migraine headache. If the first administration of nasal spray fails to abolish or reduce headache pain to a mild intensity within 30 minutes, the nasal spray is administered a second time. If the migraine headache is not abolished or reduced to a mild intensity within 90 minutes after the second administration of nasal spray, patients are allowed to take rescue medication as prescribed by one skilled in the art.

Efficacy measures are assessed daily. Subjects are asked to record the intensity of headache, absence or presence of an aura, impairment in performing daily activities, sensitivity to light and sound and any episodes of nausea and vomiting. These events are recorded at the following times: before and 0.5, 2, 4, and 24 hours after administering the nasal spray. Patients are asked to record use of rescue pain medication and the occurrence of adverse events.

After each migraine attack or at any time of the patient's or practitioner's request, a follow-up visit at the study center is scheduled. During a follow-up visit all entries on the diary are reviewed and particular questions or concerns relating to the study are discussed. Participants are asked to call in to the center within two days of experiencing a migraine attack to ensure appropriate collection of data and compliance with study protocol.

Example 13

Study of intranasal administration of oxytocin and diclofenac for the treatment of migraine. The study is conducted as described above in Example 12, forty patients suffering from migraine with or without aura are enrolled in a double-blinded, randomized, cross-over study. The total study duration is determined by the time that elapses until a patient has experienced two migraine attacks. Twenty participants are randomized to receive oxytocin and diclofenac as nasal sprays for treating the first migraine attack and to receive diclofenac nasal spray only (without oxytocin) for treating the second migraine attack. Twenty subjects are randomized to the reverse order of drug treatment.

Once a patient identifies the onset of a migraine attack, the patient is instructed to administer two puffs of diclofenac nasal spray to each nostril within 5 minutes. Each puff contains 0.2 mg diclofenac (Novartis Ophthalmics, Ga). After a five minute waiting period, two puffs of oxytocin or placebo nasal spray are administered to each nostril. Each puff contains 2 IU or 3.4 µg oxytocin (American Pharmaceutical Partners, Inc, Ill.). At the time of drug administration a moderate headache not declining in intensity should be present. Experiencing a mild headache or an aura only should not result in self-administration of drug. Nasal spray is administered no later than 2 hours after the onset of the migraine headache. If the first administration of nasal spray fails to abolish or reduce headache pain to a mild intensity within 30 minutes, the nasal spray is administered for a second time. If the migraine headache is not abolished or reduced to a mild intensity within 90 minutes after the second administration of nasal spray, patients are allowed to take rescue medication as prescribed by one skilled in the art.

Efficacy measures are assessed daily. Subjects are asked to record the intensity of headache, absence or presence of an aura, impairment in performing daily activities, sensitivity to light and sound and any episodes of nausea and vomiting. These events are recorded at the following times: before and 0.5, 2, 4, and 24 hours after administering the nasal spray.

Patients are asked to record use of rescue pain medication and the occurrence of adverse events.

After each migraine attack or at any time of the patient's or practitioner's request, a follow-up visit at the study center is scheduled. During a follow-up visit all entries on the diary are reviewed and particular questions or concerns relating to the study are discussed. Participants are asked to call in within two days of experiencing a migraine attack to ensure appropriate collection of data and compliance with study protocol.

Example 14

Sprague-Dawley rats (Charles River Laboratories) were anesthetized with isofluorane and a platinum electrode was inserted transcranially into the trigeminal ganglion. Nerve impulses (action potential) were recorded from single pain sensing nerve cells in the trigeminal ganglion in response to application of noxious laser pulses to the face of the rats. After recording responses to several identical laser pulses, 10 nmoles of oxytocin was applied to the nose of the rats. Thereafter, identical laser pulses were once again applied and recorded.

Figure 2:
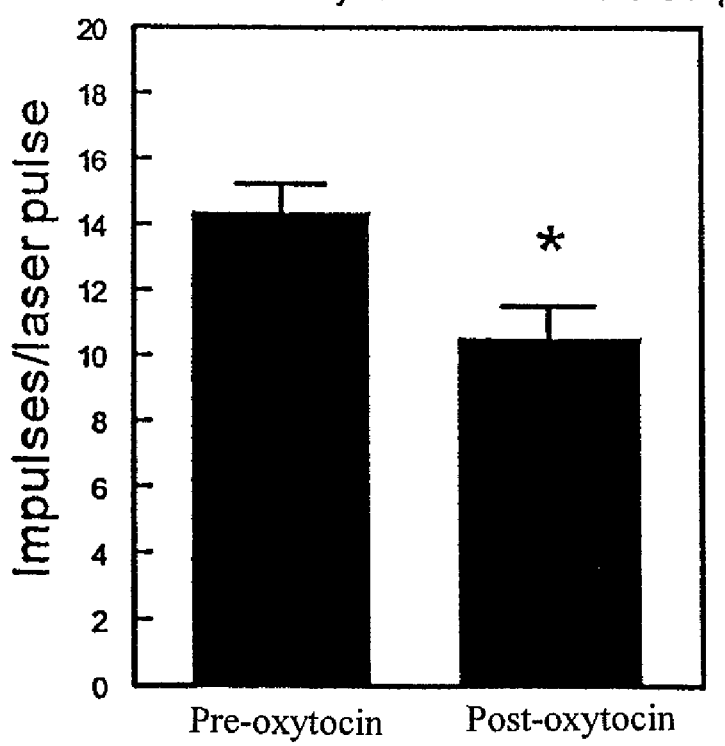
FIG. 2 depicts the effect of intranasal administration of oxytocin on trigeminal nerve impulses in response to noxious laser pulses to the face in a rat model. Data demonstrating average nerve impulses after noxious laser pulses to the face pre- and post-treatment are shown.

FIG. 2 shows the average nerve impulses per a laser pulse for pre-oxytocin and post-oxytocin treatment. Oxytocin significantly ($p<0.05$) reduced the neuronal response to noxious laser pulses applied to the animal's face. These data showed that at least part of the analgesic effect of nasal application of oxytocin was by way of direct inhibition of neurons in the trigeminal nerve.

Example 15

Male Sprague-Dawley rats (Charles River Laboratories) were anesthetized with isoflurane and used in the following experiments. In the anesthetized rats, single unit, extracellular recordings were performed in trigeminal nucleus caudalis while stimulating the ipsilateral facial skin with constant-current bipolar electrical stimulation. Epoxylate-insulated, tungsten microelectrodes (10 MOhm) were used under stereotaxic coordinate control.

FIG. 3 demonstrates the effect of intranasal oxytocin electrical stimulation-induced responses of trigeminal nucleus caudalis wide dynamic range (WDR) neurons. Shown are responses (action potentials per 30 stimuli) to repeated stimulation of a rat's face before oxytocin administration (pre-oxytocin). After administration with oxytocin at approximately 0.1 IU, responses were recorded every five minutes for 65 minutes. A second administration of oxytocin at the same dosage was administered at approximately 70 minutes after the first dose. The approximate site of the administration of the electrical stimulation is indicated by the black spot on a map of the rat's face (FIG. 3B). FIG. 3C shows raw data recorded during electrical stimulation before oxytocin administration. FIG. 3D shows raw data recorded during electrical stimulation 30 minutes after intranasal oxytocin administration.

Figure 3A:
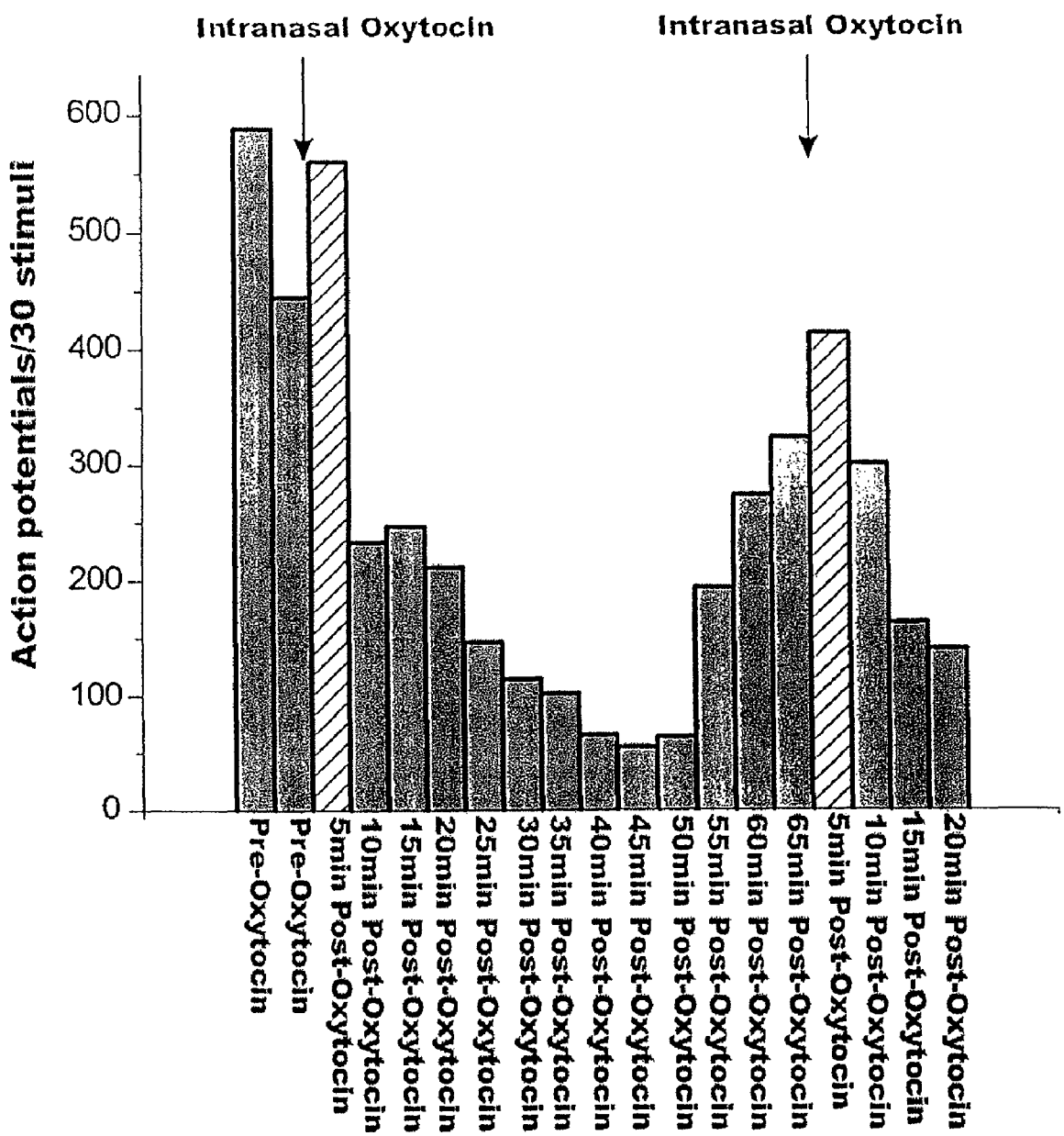
FIGS. 3A-3D depict the effect of intranasal administration of oxytocin on electrical stimulus-induced responses of trigeminal nucleus caudalis wide dynamic range neurons.
Figure 3B:
Figure 3C:
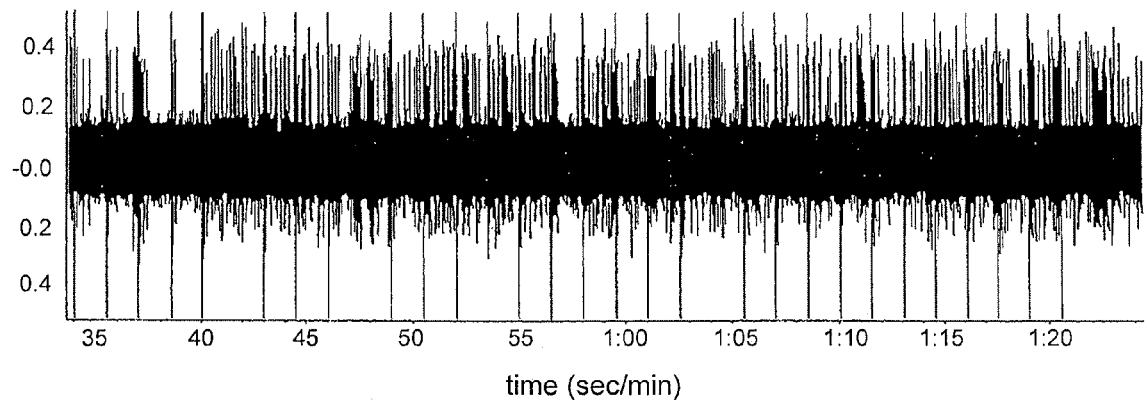
Figure 3D:
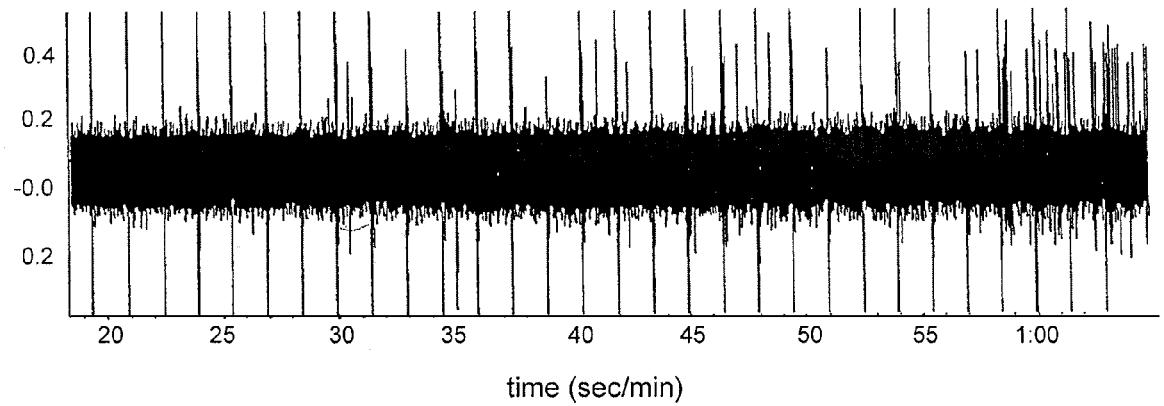

Oxytocin treatment caused a significant reduction in responses beginning 10 minutes after a first administration and continued until 50 minutes post treatment when responses began to increase (FIG. 3A). At approximately 70 minutes after the first treatment, a second dose of oxytocin was administered. Within 10 minutes, the second oxytocin treatment caused a significant reduction in responses. These data demonstrated that intranasal administration of oxytocin could cause a large effect (i.e. reduction in action potentials) but also that the effect was reproducible within a short period of time.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

All publications, patents, and patent applications cited herein are hereby incorporated by reference in their entirety.

What is claimed as new and desired to be protected by Letters Patent of the United States is:

1. A method of treating chronic head or facial pain associated with the trigeminal nerve in an individual in need thereof comprising intranasally administering to an individual in need thereof an effective dose of an oxytocin peptide, wherein the head or facial pain arises from a tension type headache, a vascular type headache, a cluster headache, infection, ingestion of a toxin, overconsumption of alcohol, hydrocephalus, trauma or intracranial disorders.

2. The method according to claim 1, wherein the head or facial pain arises from a cluster headache, a vascular type headache or a tension type headache.

3. The method according to claim 1, wherein the head or facial pain is episodic.

4. The method according to claim 1, wherein the oxytocin peptide is administered to the lower two thirds of the nasal cavity.

5. The method according to claim 1, wherein the effective dose is about 4 IU to about 24 IU.

6. The method according to claim 1, wherein the oxytocin peptide is administered as a pharmaceutical composition.

7. The method according to claim 6, wherein the pharmaceutical composition further comprises at least one additional active agent.

8. The method according to claim 6, wherein the pharmaceutical composition further comprises nociceptin/orphanin FQ.

9. The method according to claim 6, wherein the pharmaceutical composition further comprises an effective therapeutic amount of a vasoconstrictor.

10. The method according to claim 6, wherein the pharmaceutical composition further comprises one or more pharmaceutically acceptable excipients, adjuvants, diluents or stabilizers.

11. The method according to claim 6, wherein the pharmaceutical composition is administered as a powder, a gel, a film, an ointment, a liquid, a suspension, a cream or a bioadhesive.

12. The method according to claim 6, wherein the pharmaceutical composition further comprises at least one protease inhibitor or at least one absorption enhancer.

13. The method according to claim 6, wherein the pharmaceutical composition further comprises at least one protease inhibitor and at least one absorption enhancer.

14. The method according to claim 1, wherein the effective dose is about 0.1 IU to about 150 IU.

15. The method according to claim 1, wherein the effective dose is about 1 IU to about 100 IU.

16. The method according to claim 1, wherein the effective dose is about 10 IU to about 80 IU.

17. The method according to claim 1, wherein administration results in reduction of a pain rating on the VAS of 30% or more.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5

<210> SEQ ID NO 2
<211> LENGTH: 13
<212> TYPE: PRT
<213> ORGANISM: Artificial Sequence
<220> FEATURE:
<221> NAME/KEY: MYRISTATE
<222> LOCATION: (1)...(1)
<223> OTHER INFORMATION: N-myristoylation of Ser
<220> FEATURE:
<223> OTHER INFORMATION: PKC inhibitor

<400> SEQUENCE: 2

Ser Ile Tyr Arg Arg Gly Ala Arg Arg Trp Arg Lys Leu
1               5                   10
```

```
-continued

<210> SEQ ID NO 3
<211> LENGTH: 9
<212> TYPE: PRT
<213> ORGANISM: Artificial Sequence
<220> FEATURE:
<221> NAME/KEY: MOD_RES
<222> LOCATION: (4)...(4)
<223> OTHER INFORMATION: Xaa = Dpr (2,3-Diaminopropionic acid)
<220> FEATURE:
<221> NAME/KEY: AMIDATION
<222> LOCATION: (9)...(9)
<223> OTHER INFORMATION: C-terminal amidation of Tyr
<220> FEATURE:
<223> OTHER INFORMATION: peptide antagonist of pro-nociceptive peptide
      neurotransmitter recepter Y1-5

<400> SEQUENCE: 3

Ile Glu Pro Xaa Tyr Arg Leu Arg Tyr
1               5
```